US011077177B2

(12) United States Patent
Zanetti

(10) Patent No.: US 11,077,177 B2
(45) Date of Patent: *Aug. 3, 2021

(54) UNIVERSAL CANCER VACCINE

(71) Applicant: Maurizio Zanetti, La Jolla, CA (US)

(72) Inventor: Maurizio Zanetti, La Jolla, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/906,876

(22) Filed: Feb. 27, 2018

(65) Prior Publication Data

US 2018/0256691 A1  Sep. 13, 2018

Related U.S. Application Data

(62) Division of application No. 15/439,649, filed on Feb. 22, 2017, now Pat. No. 9,937,247.

(60) Provisional application No. 62/298,956, filed on Feb. 23, 2016, provisional application No. 62/320,440, filed on Apr. 8, 2016, provisional application No. 62/341,771, filed on May 26, 2016.

(51) Int. Cl.
*A61K 39/00* (2006.01)
*A61K 38/45* (2006.01)
*A61K 39/39* (2006.01)
*A61K 39/015* (2006.01)
*A61K 39/12* (2006.01)

(52) U.S. Cl.
CPC .......... *A61K 39/0005* (2013.01); *A61K 38/45* (2013.01); *A61K 39/001157* (2018.08); *A61K 39/015* (2013.01); *A61K 39/12* (2013.01); *A61K 39/39* (2013.01); *A61K 2039/6037* (2013.01); *C12N 2710/20034* (2013.01); *C12N 2760/18434* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 5,662,907 A * | 9/1997 | Kubo | C07K 14/33 424/185.1 |
| 8,697,836 B2 | 4/2014 | Zanetti | |
| 9,937,247 B2 | 4/2018 | Zanetti et al. | |
| 2002/0018806 A1 | 2/2002 | Agrawal et al. | |
| 2002/0102686 A1 | 8/2002 | Morin | |
| 2004/0086518 A1 | 5/2004 | Zanetti | |
| 2009/0202499 A1 | 8/2009 | Zanetti et al. | |
| 2010/0166787 A1* | 7/2010 | Weiner | A61K 39/0011 424/185.1 |
| 2011/0206736 A1 | 8/2011 | Waldman et al. | |
| 2013/0129760 A1 | 5/2013 | Gaudernack et al. | |
| 2014/0234351 A1 | 8/2014 | Bender et al. | |
| 2015/0004194 A1 | 1/2015 | Wang et al. | |
| 2017/0239336 A1 | 8/2017 | Zanetti | |

FOREIGN PATENT DOCUMENTS

| | | |
|---|---|---|
| CA | 2399816 A1 | 8/2001 |
| CA | 2652310 A1 | 8/2007 |
| EP | 1257284 A1 | 11/2002 |
| EP | 1993597 A2 | 11/2008 |
| JP | 2004527449 A | 9/2004 |
| WO | WO-0160391 A1 | 8/2001 |
| WO | WO-2007094924 A2 | 8/2007 |
| WO | WO-2017147160 A1 | 8/2017 |

OTHER PUBLICATIONS

Rudikoff et al. (PNAS USA, 1982, 79: 1979-1983) (Year: 1982).*
Coleman et al. (Research in Immunology, 1994; 145(1): 33-36) (Year: 1994).*
Adolevi et al., Immunogenic HLA-B 0702-restricted epitopes derived from human telomerase reverse transcriptase that elicit anti-tumor cytotoxic T-cell responses. Clin. Cancer Res.,12:3158-3167, 2006.
Bolonaki et al., Vaccination of patients with advanced no-small-cell lung cancer with an optimized cryptic human telomerase reverse transcriptase peptide. Journal of Clinical Oncology, 25(19):2727-2734, 2007.
Cortez-Gonzalez and Zanetti, Identification of immunogenic peptides of the self-tumor antigen telomerase reverse transcriptase. In "Cancer immunotherapy Methods"; P. Yotnda Ed. Book series "Methods in Molecular Biology" Chapter 12, Humana Press, USA. 651: 211-225, 2010.
Cortez-Gonzalez and Zanetti, Telomerase immunity from bench to bedside: round one. Journal of Translational Medicine, 5:12, 17 pages, 2007.
Cortez-Gonzalez et al., Immunogenic HLA B7-restricted peptides of human telomerase reverse transcriptase. Int. Immunol., 8:1707-1718, 2006.
Filaci et al., Frequency of telomerase-specific CD8+ T lymphocytes in cancer patients. Blood. 107:1505-1512, 2006.
Georgoulias et al., A Multicenter randomized Phase IIb efficacy study of Vx-001, a peptide-based cancer vaccine as maintenance treatment in advanced non-small-cell lung cancer: Treatment rationale and protocol dynamics. Clinical Lung Cancer, 14(4):461-465, 2013.
Gross et al., High vaccination efficiency of low-affinity epitopes in antitumor immunotherapy. Journal of Clinical Investigation, 113:425-433, 2004.
Hernandez et al., Antigenicity and immunogenicity of peptide analogues of a low affinity peptide of the human telomerase reverse transcriptase tumor antigen. Eur. J. Immunol., 34:2331-2341, 2004.
Hernandez et al., Identification of a human telomerase reverse transcriptase peptide of low affinity for HLA A2.1 that induces CTL and mediates lysis of tumor cells. Proc. Natl. Acad. Sci. USA, 99:12275-12280, 2002.

(Continued)

*Primary Examiner* — Misook Yu
(74) *Attorney, Agent, or Firm* — Wilson Sonsini Goodrich & Rosati

(57) ABSTRACT

Described herein are compositions of matter and methods for treating cancer. The compositions comprise altered human telomerase polypeptides containing T cell epitopes that have been altered to increase immunogenicity. The methods comprise administration of the polypeptides or nucleic acids, such as DNA or RNA encoding the polypeptides, to individuals afflicted with, or at risk of, developing cancer.

11 Claims, 5 Drawing Sheets

Specification includes a Sequence Listing.

(56) References Cited

OTHER PUBLICATIONS

Mavroudis et al., A Phase I study of the optimized cryptic peptide TERT572y in patients with advanced mailignancies. Oncology, 70:306-314, 2006.
Minev et al., Cytotoxic T cell immunity against telomerase reverse transcriptase in humans. PNAS, 97(9):4796-4801, 2000.
PCT/US2017/018895 International Search Report and Written Opinion dated Jul. 17, 2017.
Rapoport et al., Combination immunotherapy using adoptive T-cell transfer and tumor antigen vaccination on the basis of hTERT and surviving after ASCT for myeloma. Blood, 117(3):788-797, 2011.
Schroers et al., Human telomerase reverse transcriptase-specific T-helper responses induced by promiscuous major histocompatibility complex class II-restricted epitopes. Clinical Cancer Research, 9:4743-4755, 2003.
U.S. Appl. No. 15/439,649 Office Action dated Aug. 8, 2017.
Vetsika et al., Sequential administration of the native TERT572 cryptic peptide enhances the immune response initiated by its optimized variant TERT572y in cancer patients. J. Immunotherapy, 34:641-650, 2011.
Zanetti, A second chance for telomerase reverse transcriptase in anticancer immunotherapy. Nature Reviews, Clinical Oncology, Advanced Online Publication, 14 pages, 2016.
Zanetti et al., Telomerase reverse transcriptase as target of anti-tumor T cell responses in humans. Springer Sem. Immunopathol., 27: 87-104, 2005.
PCT/US2017/018895 International Preliminary Report on Patentability dated Sep. 20, 2018.

\* cited by examiner

UNIVERSAL CANCER VACCINE

CROSS REFERENCE

This application is a divisional of U.S. application Ser. No. 15/439,649 filed Feb. 22, 2017, issued as U.S. Pat. No. 9,937,247, which claims priority to U.S. Application Ser. Nos. 62/298,956 filed on Feb. 23, 2016; 62/320,440 filed on Apr. 8, 2016; and 62/341,771 filed on May 26, 2016; all of which are incorporated herein in their entirety.

SEQUENCE LISTING

The instant application contains a Sequence Listing which has been submitted electronically in ASCII format and is hereby incorporated by reference in its entirety. Said ASCII copy, created on Mar. 28, 2017 is named 50029701201_SL.txt and is 39,970 bytes in size.

BACKGROUND

Human telomerase reverse transcriptase (TERT) is a constitutive self-tumor antigen and a potential target for cancer immunotherapy. In the past immunotherapy trials targeting TERT have failed to deliver on the promise of TERT as an immunotherapy target. For example, of 25 clinical studies performed using TERT as an antigen to induce an anti-tumor immune response, an objective clinical response has been shown in only 2 studies, and even then, with an overall response rate of less than 20%.

Telomerase reverse transcriptase (TERT) is a component of telomerase, the unique cellular enzyme that synthesizes the tandem 5'-TTAGGG-3' exonucleotide repeats of telomeric DNA by reverse transcription of its own RNA template (TERC). The discovery of telomerase and telomerase-mediated extension of telomeric DNA solved both the end-replication problem, i.e., the mechanism by which telomeric DNA is maintained, and the end-protection problem. Human TERT is a self-antigen that consists of ~1130 amino acids. In humans, telomerase activity by the canonical telomeric repeat amplification protocol (TRAP) assay is detected in >85% of tumors of various histological type, but not in normal tissues.

Tolerance is one major determinant in the development of one's individual immune response, and a major obstacle to develop immunotherapy to self-antigens such as telomerase. During ontogeny, tolerance shapes the repertoire by eliminating high affinity T cell precursors and sparing low affinity T cell precursors. Tumor growth can also promote peripheral tolerance if antigen-presenting cells activate T cells in the absence of costimulatory molecules (signal 2). In addition, certain T cell specificities may be lost over time due to senescence and exhaustion, or by remodeling cancer cell immunogenicity by immune editing.

Cellular responses to antigen by B and T cells are largely dictated by the human leukocyte antigens (HLA) present on an individual's cell surface. Intracellular antigens (e.g., viral proteins, self-proteins) are processed intracellularly, generally by the proteasome, to yield 8-10 amino acid polypeptides. 8-10-mers are loaded onto MHC class I HLA subtype A, B and C molecules for presentation to cytotoxic CD 8+ T cells. These cytotoxic T cells can then recognize and destroy cells carrying organisms (e.g., viruses) that express the protein. There are thousands of different HLA alleles split between the A, B and, C locus. These alleles are grouped into different types with designations such as A2 or B44. Some types are more common than others, with the A2 type being the most prevalent.

SUMMARY

Telomerase is expressed at many stages of tumor development, as shown in FIG. 1. Additionally, telomerase promoter mutations are seen in many different cancer types. See FIG. 2. Thus telomerase is an attractive target for therapeutic intervention including, among others, vaccination with the polypeptides described herein. Alternatively, T cells can be stimulated ex vivo or in vivo by antigen presenting cells loaded with T cell response epitopes derived form the altered human telomerase polypeptides described herein. By altering a low affinity T cell epitope to promote binding to a particular HLA as shown in FIG. 3A it is possible to circumvent the problem of tolerance as previously described. FIG. 3B illustrates that this approach is feasible for a polypeptide corresponding to SEQ ID NO: 13 which substitutes an arginine for tyrosine mutation at p1 of the polypeptide that binds to HLA-A2 (position 572 of wild type telomerase).

Referring to FIGS. 4 and 5 (two different not limiting schematics of an altered human telomerase polypeptide), telomerase possess several potential HLA binding polypeptides (rectangles) that can be altered (black squares) to bind to HLA with a much stronger affinity than the wild type version. If administered with a T cell helper epitope (diamonds), e.g., by engineering such an epitope into the altered telomerase, the altered telomerase peptides can induce a CD8+ T cell response. Because these peptides originally bind to various HLA alleles with low to medium affinity the endogenous CD 8+ T cell repertoire against them is not yet tolerized. Administering an altered telomerase that has one or more altered polypeptides will activate and expand these untolerized T cells leading to an immune response to telomerase expressing (e.g., cancer) cells.

Described herein, are compositions and methods useful for the immunotherapy of cancer using altered telomerase or altered telomerase polypeptides as an antigen. The compositions are useful because they break tolerance to the self-antigen telomerase, and because they are capable of prompting a response in individuals of differing HLA haplotype. In certain embodiments, the composition comprises one or more HLA binding polypeptides, derived from human telomerase, which have been altered from their naturally occurring sequence to impart increased immunogenicity. These altered polypeptides are generally subdominant, and as such, T cells responsive to them have not been tolerized. In certain embodiments, the polypeptides are administered separately or as a single larger polypeptide. In certain, embodiments, the polypeptides are administered with a T helper epitope, adjuvant, or ligand for an innate immune activating molecule, such as a Toll-like receptor (TLR) or NOD-like receptor (NLR). Also described herein, are nucleic acids that encode telomerase and T helper cell polypeptides including RNAs.

In certain embodiments, described herein is, a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least two different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least three different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least five different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least ten different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least seven different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, wherein each of the seven different sequences binds a different human leukocyte antigen selected from the group consisting of A1, A2, A3, A11, A24, B3, B7 and B44. In certain embodiments, the polypeptide comprises a non-human T cell helper epitope, wherein the non-human T cell helper epitope binds more than one human class II HLA type. In certain embodiments, the T cell helper epitope comprises tetanus toxoid. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, the polypeptide comprises a total length of at least 20 amino acids. In certain embodiments, the polypeptide comprises a total length of at least 50 amino acids. In certain embodiments, the polypeptide comprises a total length of at least 100 amino acids. In certain embodiments, a nucleic acid molecule encodes the polypeptide. In certain embodiments, a complex comprising at least 8 contiguous amino acids of the polypeptide is bound to a cell surface human leukocyte antigen of an antigen presenting cell. In certain embodiments, the antigen presenting cell is a B cell. In certain embodiments, the antigen presenting cell is a dendritic cell. In certain embodiments, described herein, is a composition that comprises the polypeptide and an immunological adjuvant. In certain embodiments, described herein, is a composition that comprises the polypeptide and a Toll-like receptor ligand. In certain embodiments, described herein, is a composition that comprises the polypeptide and a pharmaceutically acceptable vehicle, carrier, excipient, or a combination thereof. In certain embodiments, described herein, is a composition that comprises the polypeptide and a non-human T cell helper epitope, wherein the non-human T cell helper epitope binds more than one human class II HLA type. In certain embodiments, the T cell helper epitope comprises tetanus toxoid. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In another embodiment, described herein, is an altered human telomerase polypeptide with at least 90% identity to the sequence set forth in SEQ ID NO: 1, wherein the altered human telomerase polypeptide comprises at least one amino acid substitution that is at position R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide is at least 95% identical to SEQ ID NO: 1. In certain embodiments, the altered human telomerase polypeptide comprises at least two amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least three amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least five amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least ten amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, at least one amino acid substitution increases the binding affinity of an 8 to 10 amino acid polypeptide derived from the altered human telomerase polypeptide to at least one human leukocyte antigen of an A, B, or C type by at least two-fold. In certain embodiments, at least one amino acid substitution increases the binding affinity of an 8 to 10 amino acid polypeptide derived from the altered human telomerase polypeptide to at least one human leukocyte antigen of an A, B, or C type by at least five-fold. In certain embodiments, at least one amino acid substitution increases the binding affinity of an 8 to 10 amino acid polypeptide derived from the altered human telomerase polypeptide to at least one human leukocyte antigen of an A, B, or C type by at least ten-fold. In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the T cell helper epitope comprises tetanus toxoid. In certain embodiments, the T cell helper epitope is selected from the group consisting of SEQ ID NO: 30 to SEQ ID NO:

55, and combinations thereof. In certain embodiments, the T cell helper epitope is set forth in SEQ ID NO: 30. In certain embodiments, a nucleic acid molecule encodes the altered human telomerase polypeptide. In certain embodiments, a complex comprising at least 8 contiguous amino acids of the altered human telomerase polypeptide is bound to a cell surface human leukocyte antigen of an antigen presenting cell. In certain embodiments, the antigen presenting cell is a B cell. In certain embodiments, the antigen presenting cell is a dendritic cell. In certain embodiments, described herein, is a composition that comprises the altered human telomerase polypeptide and an immunological adjuvant. In certain embodiments, described herein, is a composition that comprises the altered human telomerase polypeptide and a Toll-like receptor ligand. In certain embodiments, described herein, is a composition that comprises the altered human telomerase polypeptide and a pharmaceutically acceptable vehicle, carrier, excipient, or a combination thereof. In certain embodiments, described herein, is a composition that comprises the altered human telomerase polypeptide and a non-human T cell helper epitope, wherein the non-human T cell helper epitope binds more than one human class II HLA type. In certain embodiments, the T cell helper epitope comprises tetanus toxoid. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In another embodiment, described herein, is an altered human telomerase polypeptide with at least 90% identity to the sequence set forth in SEQ ID NOs: 28 or 29, wherein the altered human telomerase polypeptide is not identical to SEQ ID NO: 1. In certain embodiments, the altered human telomerase polypeptide is at least 95% identical to SEQ ID NO: 28 or 29. In certain embodiments, the altered human telomerase polypeptide is at least 98% identical to SEQ ID NO: 28 or 29. In certain embodiments, the altered human telomerase polypeptide is at least 99% identical to SEQ ID NO: 28 or 29. In certain embodiments, the altered human telomerase polypeptide is at least 100% identical to SEQ ID NO: 28 or 29. In certain embodiments, the altered telomerase polypeptide increases the binding affinity of an 8-10 amino acid polypeptide derived from the altered human telomerase polypeptide to at least one human leukocyte antigen of the A, B, or C type by at least two-fold. In certain embodiments, the at least one amino acid alteration increases the binding affinity of an 8-10 amino acid polypeptide derived from the altered human telomerase polypeptide to at least one human leukocyte antigen of the A, B, or C type by at least five-fold. In certain embodiments, the at least one amino acid alteration increases the binding affinity of an 8-10 amino acid polypeptide derived from the altered human telomerase polypeptide to at least one human leukocyte antigen of the A, B, or C type by at least ten-fold. In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, a nucleic acid molecule encodes the altered human telomerase polypeptide. In certain embodiments, a complex comprising at least 8 contiguous amino acids of the altered human telomerase polypeptide is bound to a cell surface human leukocyte antigen of an antigen presenting cell. In certain embodiments, the antigen presenting cell is a B cell. In certain embodiments, the antigen presenting cell is a dendritic cell. In certain embodiments, described herein, is a composition that comprises the altered human telomerase polypeptide and an immunological adjuvant. In certain embodiments, described herein, is a composition that comprises the altered human telomerase polypeptide and a Toll-like receptor ligand. In certain embodiments, described herein, is a composition that comprises the altered human telomerase polypeptide and a pharmaceutically acceptable vehicle, carrier, excipient, or a combination thereof. In certain embodiments, described herein, is a composition that comprises the altered human telomerase polypeptide and a non-human T cell helper epitope, wherein the non-human T cell helper epitope binds more than one human class II HLA type. In certain embodiments, the T cell helper epitope comprises tetanus toxoid. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In certain embodiments, described herein, is a method for treating an individual with cancer the method comprising administering to an individual with cancer a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least two different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least three different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least five different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least ten different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least seven different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, wherein each of the seven different sequences binds a different human leukocyte antigen selected from the group consisting of A1, A2, A3, A11, A24, B3, B7 and B44. In certain embodiments, the polypeptide comprises a non-human polypeptide comprising a T cell helper epitope, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, the polypeptide comprises a total length of at least 20 amino acids. In certain embodiments, the polypeptide comprises a total length of at least 50 amino acids. In certain embodiments, the polypeptide comprises a total length of at least 100 amino acids. In certain embodiments, a nucleic acid molecule is administered that encodes the polypeptide. In certain embodiments, the method comprises administering a complex comprising at least 8 contiguous amino acids of the polypeptide bound to a cell surface human leukocyte antigen of an antigen presenting cell. In certain embodiments, the antigen presenting cell is a B cell. In certain embodiments, the antigen presenting cell is a dendritic cell. In certain embodiments, the method further comprises administering an immunological adjuvant. In certain embodiments, the method further comprises administering a Toll-like receptor ligand. In certain embodiments, the method further comprises administering a pharmaceutically acceptable vehicle, carrier, excipient, or a combination thereof. In certain embodiments, the cancer is of hematological origin. In certain embodiments, the individual in need has a telomerase positive cancer. In certain embodiments, the cancer is selected from the group consisting of bladder cancer, liver cancer, glioblastoma, melanoma, prostate cancer, a cancer of the thymus, cancer of the thyroid, and kidney cancer. In certain embodiments, the method further comprises administering a non-human T cell helper epitope. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In certain embodiments, described herein, is a method for treating an individual with cancer comprising administering to an individual with cancer an altered human telomerase polypeptide with at least 90% identity to the sequence set forth in SEQ ID NO: 1, wherein the altered human telomerase polypeptide comprises at least one amino acid substitution that is at position R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide is at least 95% identical to SEQ ID NO: 1. In certain embodiments, the altered human telomerase polypeptide comprises at least two amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least three amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least five amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least ten amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the at least one amino acid substitution increases the binding affinity of an 8-10 amino acid polypeptide derived from the altered human telomerase polypeptide to at least one human leukocyte antigen of an A, B, or C type by at least two-fold. In certain embodiments, the at least one amino acid substitution increases the binding affinity of an 8-10 amino acid polypeptide derived from the altered human telomerase polypeptide to at least one human leukocyte antigen of an A, B, or C type by at least five-fold. In certain embodiments, the at least one amino acid substitution increases the binding affinity of an 8-10 amino acid polypeptide derived from the altered human telomerase polypeptide to at least one human leukocyte antigen of an A, B, or C type by at least ten-fold. In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the T cell helper epitope is selected from the group consisting of SEQ ID NO: 30 to SEQ ID NO: 55, and combinations thereof, wherein the non-human T cell helper epitope binds more than one human class II HLA type. In certain embodiments, the T cell helper epitope is set forth in SEQ ID NO: 30. In certain embodiments, a nucleic acid molecule is administered that encodes the altered human telomerase polypeptide. In certain embodiments, the method comprises administering a complex comprising at least 8 contiguous amino acids of the polypeptide bound to a cell surface human leukocyte antigen of an antigen presenting cell. In certain embodiments, the antigen presenting cell is a B cell. In certain embodiments, the antigen presenting cell is a dendritic cell. In certain embodiments, the method further comprises administering an immunological adjuvant. In certain embodiments, the method further comprises administering a Toll-like receptor ligand. In certain embodiments, the method further comprises administering a pharmaceutically acceptable vehicle, carrier, excipient, or a combination thereof. In certain embodiments, the cancer is of hematological origin. In certain embodiments, the individual in need has a telomerase positive cancer. In certain embodiments, the cancer is selected from the group consisting of bladder cancer, liver cancer, glioblastoma, melanoma, prostate cancer, a cancer of the thymus, cancer of the thyroid, and kidney cancer. In certain embodiments, the method further comprises administering a non-human T cell helper epitope. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In certain embodiments, described herein, is a method for treating an individual with cancer the method comprising administering to the individual with cancer an altered human telomerase polypeptide at least 90% identical to SEQ ID NO: 28 or 29, wherein the altered human telomerase polypeptide is not identical to SEQ ID NO: 1. In certain embodiments, the altered human telomerase polypeptide is at least 95% identical to SEQ ID NO: 28 or 29. In certain embodiments, the altered human telomerase polypeptide is at least 98% identical to SEQ ID NO: 28 or 29. In certain embodiments, the altered human telomerase polypeptide is at least 99% identical to SEQ ID NO: 28 or 29. In certain embodiments, the altered human telomerase polypeptide is at least 100% identical to SEQ ID NO: 28 or 29. In certain embodiments, the altered telomerase polypeptide increases the binding affinity of an 8-10 amino acid polypeptide derived from the altered human telomerase polypeptide to at least one human leukocyte antigen of the A, B, or C type by at least two-fold. In certain embodiments, the at least one amino acid alteration increases the binding affinity of an 8-10 amino acid polypeptide derived from the altered human telomerase polypeptide to at least one human leukocyte antigen of the A, B, or C type by at least five-fold. In certain embodiments, the at least one amino acid alteration increases the binding affinity of an 8-10 amino acid polypeptide derived from the altered human telomerase polypeptide to at least one human leukocyte antigen of the A, B, or C type by at least ten-fold. In certain embodiments, the altered human telomerase polypeptide comprises an insertion of a non-human polypeptide comprising a T cell helper epitope into the polypeptide sequence of the altered human telomerase, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, a nucleic acid molecule is administered that encodes the altered human telomerase polypeptide. In certain embodiments, the method comprises administering a complex comprising at least 8 contiguous amino acids of the polypeptide bound to a cell surface human leukocyte antigen of an antigen presenting cell. In certain embodiments, the antigen presenting cell is a B cell. In certain embodiments, the antigen presenting cell is a dendritic cell. In certain embodiments, the method further comprises administering an immunological adjuvant. In certain embodiments, the method further comprises administering a Toll-like receptor ligand. In certain embodiments, the method further comprises administering a pharmaceutically acceptable vehicle, carrier, excipient, or a combination thereof. In certain embodiments, the cancer is of hematological origin. In certain embodiments, the individual in need has a telomerase positive cancer. In certain embodiments, the cancer is selected from the group consisting of bladder cancer, liver cancer, glioblastoma, melanoma, prostate cancer, a cancer of the thymus, cancer of the thyroid, and kidney cancer. In certain embodiments, the method further comprises administering a non-human T cell helper epitope. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30.

In certain embodiments, described herein, is a method of preparing a cancer treatment the method comprising admixing a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, and a pharmaceutically acceptable vehicle, carrier, excipient, or combination thereof. In certain embodiments, the polypeptide comprises at least two different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least three different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least five different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least ten different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least seven different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, wherein each of the seven different sequences binds a different human leukocyte antigen selected from the group consisting of A1, A2, A3, A11, A24, B3, B7 and B44. In certain embodiments, the polypeptide comprises a non-human T cell helper epitope, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, the polypeptide comprises a total length of at least 20 amino acids. In certain embodiments, the polypeptide comprises a total length of at least 50 amino acids. In certain embodiments, the polypeptide comprises a total length of at least 100 amino acids. In certain embodiments, the method comprises admixing a nucleic acid molecule encoding the polypeptide, and a pharmaceutically acceptable vehicle, carrier, excipient, or combination thereof. In certain embodiments, the method comprises admixing a complex comprising at least 8 contiguous amino acids of the polypeptide bound to a cell surface human leukocyte antigen of an antigen presenting cell, and a pharmaceutically acceptable vehicle, carrier, excipient, or combination thereof. In certain embodiments, the antigen presenting cell is a B cell. In certain embodiments, the antigen presenting cell is a dendritic cell. In certain embodiments, the treatment further comprises admixing an immunological adjuvant. In certain embodiments, the treatment further comprises admixing a Toll-like receptor ligand. In certain embodiments, the treatment further comprises admixing a non-human a T cell helper epitope. In certain embodiments, the T cell helper epitope is selected from the group consisting of SEQ ID NO: 30 to SEQ ID NO: 55, and combinations thereof, wherein the non-human T cell helper epitope binds more than one human class II HLA type. In certain embodiments, the T cell helper epitope is set forth in SEQ ID NO: 30.

In certain embodiments, described herein, is a method of preparing a cancer treatment the method comprising admixing a composition comprising an altered human telomerase polypeptide with at least 90% identity to that set forth in SEQ ID NO: 1, comprising at least one amino acid substitution that is at position R19, L22, R132, L152, D444, K492, E555, L556, T564, R572, R577, D637, L675, E727, R742, T765, R811, L840, G847, T874, L940, K981, V997, or P1020, and a pharmaceutically acceptable vehicle, carrier, excipient, or combination thereof. In certain embodiments, the altered human telomerase polypeptide is at least 95% identical to SEQ ID NO: 1. In certain embodiments, the altered human telomerase polypeptide comprises at least two amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least three amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least five amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises at least ten amino acid substitutions that are at positions R19, L22, R132, L152, D444, K492, E555, L556, T564, R572, R577, D637, L675, E727, R742, T765, R811, L840, G847, T874, L940, K981, V997, or P1020. In certain embodiments, the at least one amino acid substitution increases the binding affinity of an 8 to 10 amino acid polypeptide derived from the altered human telomerase polypeptide to at least one human leukocyte antigen of an A, B, or C type by at least two-fold. In certain embodiments, the at least one amino acid substitution increases the binding affinity of an 8 to 10 amino acid polypeptide derived from the altered human telomerase polypeptide to at least one human leukocyte antigen of an A, B, or C type by at least five-fold. In certain embodiments, the at least one amino acid substitution increases the binding affinity of an 8 to 10 amino acid polypeptide derived from the altered human telomerase polypeptide to at least one human leukocyte antigen of an A, B, or C type by at least ten-fold. In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, the method comprises admixing a nucleic acid molecule encoding the altered human telomerase polypeptide, and a pharmaceutically acceptable vehicle, carrier, excipient, or combination thereof. In certain embodiments, the method comprises admixing a complex comprising at least 8 contiguous amino acids of the polypeptide bound to a cell surface human leukocyte antigen of an antigen presenting cell, and a pharmaceutically acceptable vehicle, carrier, excipient, or combination thereof. In certain embodiments, the antigen presenting cell is a B cell. In certain embodiments, the antigen presenting cell is a dendritic cell. In certain embodiments, the treatment further comprises admixing an immunological adjuvant. In certain embodiments, the treatment further comprises admixing a Toll-like receptor ligand. In certain embodiments, the treatment further comprises admixing a non-human a T cell helper epitope. In certain embodiments, the T cell helper epitope is selected from the group consisting of SEQ ID NO: 30 to SEQ ID NO: 55, and combinations thereof, wherein the non-human T cell helper epitope binds more than one human class II HLA type. In certain embodiments, the T cell helper epitope is set forth in SEQ ID NO: 30.

In certain embodiments, described herein, is a method of preparing a cancer treatment the method comprising admixing an altered human telomerase polypeptide at least 90% identical to SEQ ID NO: 28 or 29, wherein the altered human telomerase polypeptide is not identical to SEQ ID NO: 1 and a pharmaceutically acceptable vehicle, carrier, excipient, or combination thereof. In certain embodiments, the altered human telomerase polypeptide is at least 95% identical to SEQ ID NO: 28 or 29. In certain embodiments, the altered human telomerase polypeptide is at least 98% identical to SEQ ID NO: 28 or 29. In certain embodiments, the altered human telomerase polypeptide is at least 99% identical to SEQ ID NO: 28 or 29. In certain embodiments, the altered human telomerase polypeptide is at least 100% identical to SEQ ID NO: 28 or 29. In certain embodiments, the altered telomerase polypeptide increases the binding affinity of an 8 to 10 amino acid polypeptide derived from the altered human telomerase polypeptide to v the at least one amino acid alteration increases the binding affinity of an 8 to 10 amino acid polypeptide derived from the altered human telomerase polypeptide to at least one human leukocyte antigen of the A, B, or C type by at least five-fold. In certain embodiments, the at least one amino acid alteration increases the binding affinity of an 8 to 10 amino acid polypeptide derived from the altered human telomerase polypeptide to at least one human leukocyte antigen of the A, B, or C type by at least ten-fold. In certain embodiments, the altered human telomerase polypeptide comprises an insertion of a non-human polypeptide comprising a T cell helper epitope into the polypeptide sequence of the altered human telomerase, wherein the non-human T cell helper epitope binds more than one human class II HLA type. In certain embodiments, the T cell helper epitope is selected from the group consisting of SEQ ID NO: 30 to SEQ ID NO: 55, and combinations thereof. In certain embodiments, the T cell helper epitope is set forth in SEQ ID NO: 30. In certain embodiments, the method comprises admixing a nucleic acid molecule encoding the altered human telomerase polypeptide, and a pharmaceutically acceptable vehicle, carrier, excipient, or combination thereof. In certain embodiments, the method comprises admixing a complex comprising at least 8 contiguous amino acids of the polypeptide bound to a cell surface human leukocyte antigen of an antigen presenting cell, and a pharmaceutically acceptable vehicle, carrier, excipient, or combination thereof. In certain embodiments, the antigen presenting cell is a B cell. In certain embodiments, the antigen presenting cell is a dendritic cell. In certain embodiments, the treatment further comprises admixing an immunological adjuvant. In certain embodiments, the treatment further comprises admixing a Toll-like receptor ligand. In certain embodiments, the treatment further comprises admixing a non-human a T cell helper epitope. In certain embodiments, the T cell helper epitope is selected from the group consisting of SEQ ID NO: 30 to SEQ ID NO: 55, and combinations thereof, wherein the non-human T cell helper epitope binds more than one human class II HLA type. In certain embodiments, the T cell helper epitope is set forth in SEQ ID NO: 30.

In certain embodiments, described herein, is a method of treating cancer comprising transfecting an antigen presenting cell ex vivo with a nucleic acid that encodes a polypeptide of any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, SEQ ID NO: 27, SEQ ID NO: 28, or SEQ ID NO: 29. In certain embodiments, the antigen presenting cell is a B cell. In certain embodiments, the antigen presenting cell is a dendritic cell.

In certain embodiments, described herein, is a method of treating cancer comprising administering an antigen presenting cell that has been transfected ex vivo with a nucleic acid that encodes a polypeptide of any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, SEQ ID NO: 27, SEQ ID NO: 28, or SEQ ID NO: 29. In certain embodiments, the antigen presenting cell is a B cell. In certain embodiments, the antigen presenting cell is a dendritic cell. In certain embodiments, greater than $1 \times 10^6$ cells are administered. In certain embodiments, the cells are administered intravenously.

In a certain aspect provided herein, is a polypeptide comprising at least two sequences set forth in any one of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27. In certain embodiments, the polypeptide comprises at least seven different sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, wherein each of the seven different sequences binds a different human leukocyte antigen selected from the group consisting of A1, A2, A3, A11, A24, B3, B7, and B44. In certain embodiments, the polypeptide comprises a non-human T cell helper epitope, wherein the non-human T cell helper epitope binds more than one human class II HLA type. In certain embodiments, the polypeptide comprises a total length of at least 20 amino acids. In certain embodiments, the polypeptide is encoded by a polynucleotide. In certain embodiments, the polynucleotide comprises ribonucleic acid (RNA). In certain embodiments, at least eight contiguous amino acids of the polypeptide is bound to a cell surface human leukocyte antigen of an antigen presenting cell. In certain embodiments, the polypeptide further comprises an immunological adjuvant. In certain embodiments, the polypeptide further comprises a pharmaceutically acceptable vehicle, carrier or excipient. In certain embodiments, the polypeptide is for use in treating an individual with cancer.

In a certain aspect provided herein, is an altered human telomerase polypeptide with at least 90% identity to the sequence set forth in SEQ ID NO: 1, wherein the altered human telomerase polypeptide comprises at least one amino acid substitution that is at position R19, L22, R132, L152, D444, K492, E555, L556, T564, R572, R577, D637, L675, E727, R742, T765, R811, L840, G847, T874, L940, K981, V997, or P1020. In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the altered human telomerase polypeptide is encoded by a polynucleotide. In certain embodiments, the altered human telomerase polynucleotide comprises ribonucleic acid (RNA). In certain embodiments, at least eight contiguous amino acids of the altered human telomerase polypeptide is bound to a cell surface human leukocyte antigen of an antigen presenting cell. In certain embodiments, the altered human telomerase polypeptide further comprises an immunological adjuvant. In certain embodiments, the altered human telomerase polypeptide further comprises a pharmaceutically acceptable vehicle, carrier or excipient. In certain embodiments, the altered human telomerase polypeptide is for use in treating an individual with cancer.

In a certain aspect provided herein, is an altered human telomerase polypeptide with at least 90% identity to the sequence set forth in any one of SEQ ID NOs: 28 or 29, wherein the altered human telomerase polypeptide is not identical to SEQ ID NO: 1 In certain embodiments, the altered human telomerase polypeptide comprises an insertion of a non-human T cell helper epitope into the polypeptide sequence of the altered human telomerase, wherein the non-human T cell helper epitope binds more than one human class II HLA type. In certain embodiments, the altered human telomerase polypeptide is encoded by a polynucleotide. In certain embodiments, the altered human telomerase polynucleotide comprises ribonucleic acid (RNA). In certain embodiments, at least eight contiguous amino acids of the altered human telomerase polypeptide is bound to a cell surface human leukocyte antigen of an antigen presenting cell. In certain embodiments, the altered human telomerase polypeptide further comprises an immunological adjuvant. In certain embodiments, the altered human telomerase polypeptide further comprises a pharmaceutically acceptable vehicle, carrier or excipient. In certain embodiments, the altered human telomerase polypeptide is for use in treating an individual with cancer.

DETAILED DESCRIPTION OF THE INVENTION

Figure 1:
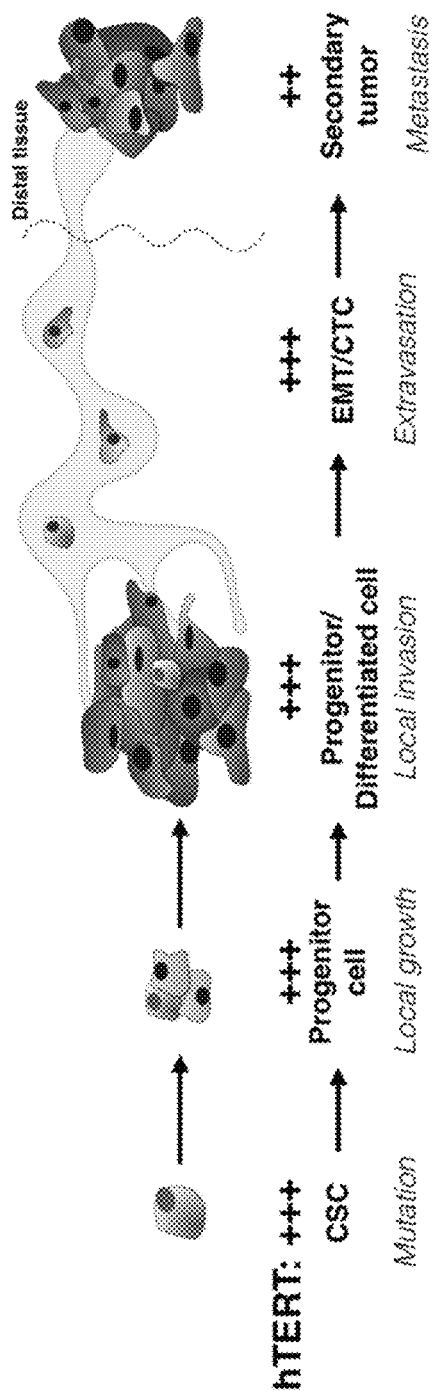
FIG. 1 is a schematic showing that telomerase is expressed at many different stage of cancer progression.
Figure 2:
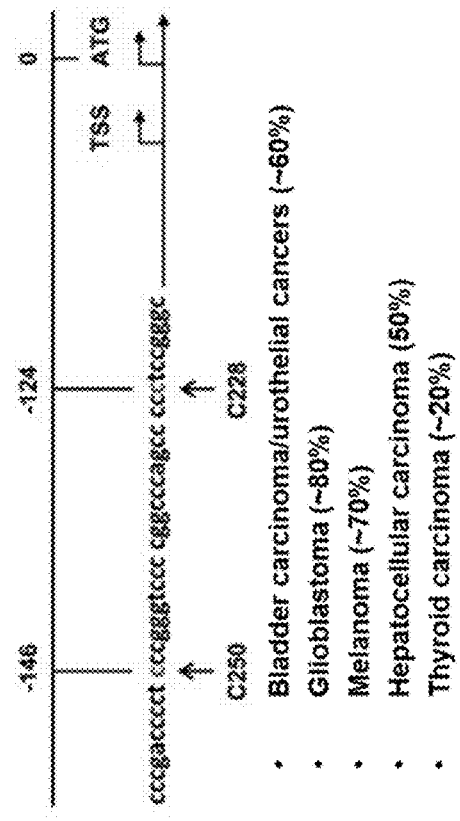
FIG. 2 is a diagram showing that many different types of cancers are caused by mutations in the telomerase promotor set forth in SEQ ID NO: 56.
Figure 3A:
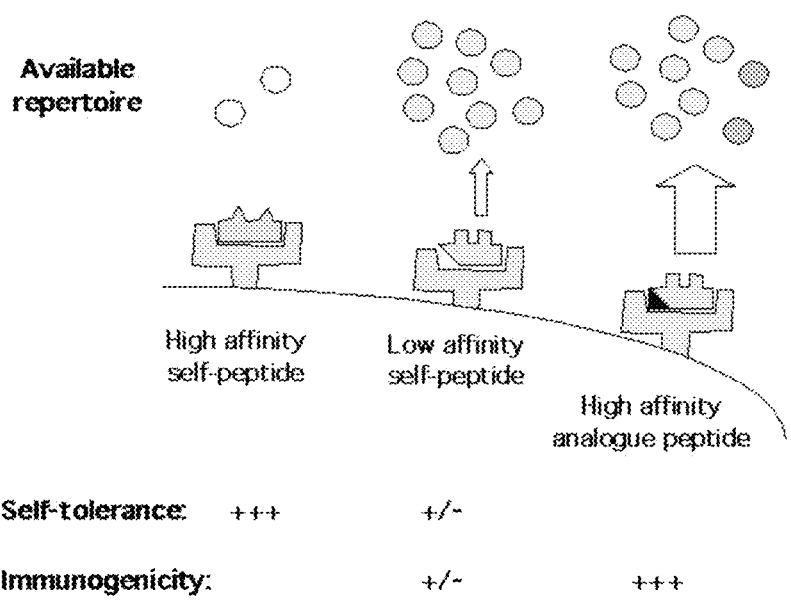
FIG. 3A shows a graphical depiction illustrating that peptides that naturally bind MHC Class I HLA subtypes with low affinity possess a T cell repertoire that has not been deleted or tolerized.
Figure 3B:
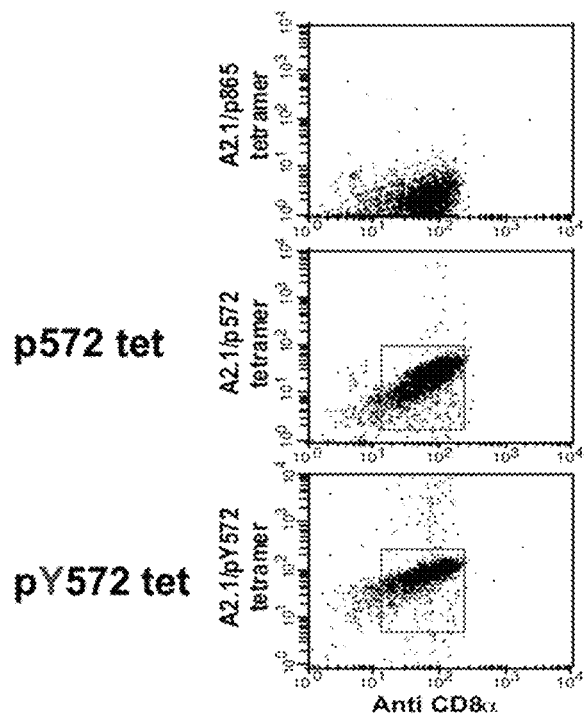
FIG. 3B shows flow cytometry data of tetramer staining of peripheral blood mononuclear cells. This data shows that immunization with an altered peptide can expand a CD 8+ T cell repertoire that cross reacts with the naturally occurring peptide.
Figure 4:
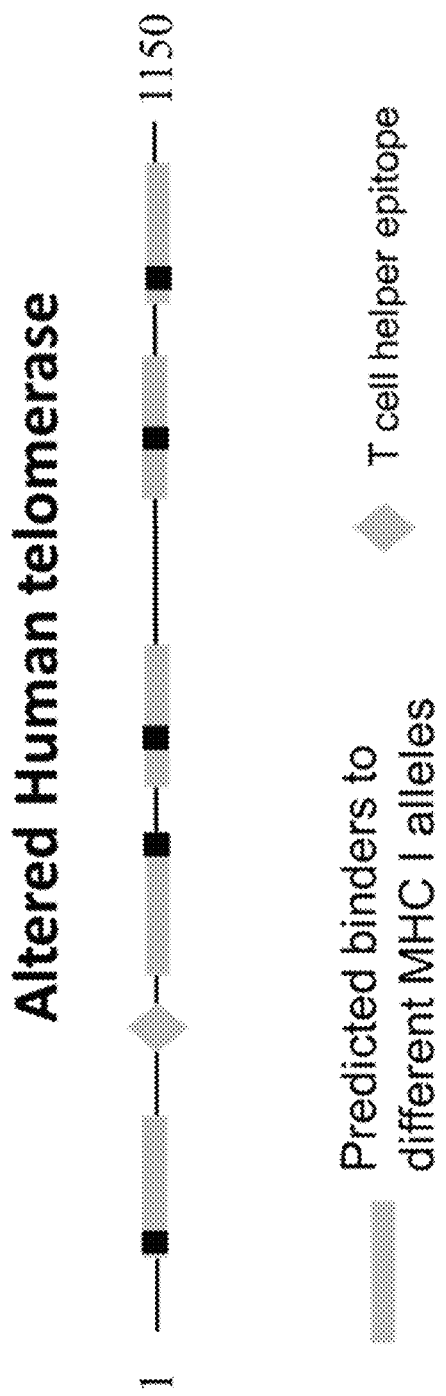
FIG. 4 is a non-limiting schematic of an altered telomerase peptide, depicting a plurality of altered epitopes, and an integrated non-human T cell helper epitope able to bind a plurality of human MHC class II HLA types.
Figure 5:
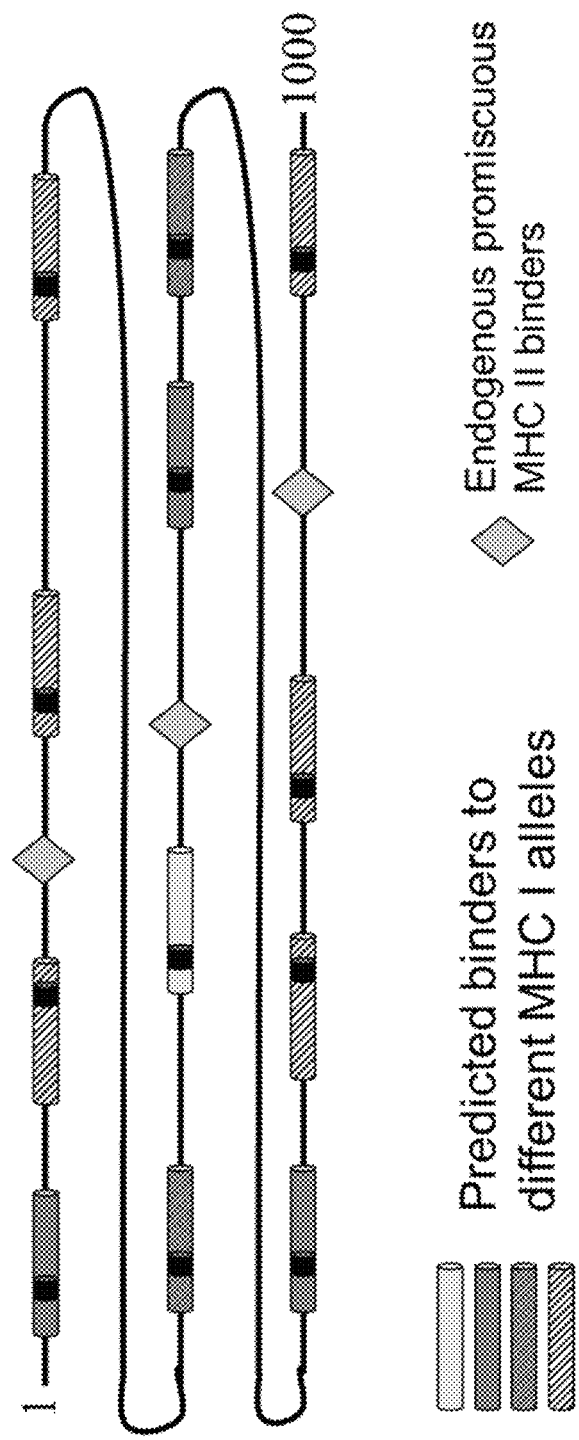
FIG. 5 is a second non-limiting schematic of an altered telomerase peptide, depicting a plurality of altered epitopes, and an integrated non-human T cell helper epitope able to bind a plurality of human MHC class II HLA types.

Described herein, in certain embodiments, is a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27.

Described herein, in certain embodiments, is an altered human telomerase polypeptide with at least 90% identity to the sequence set forth in SEQ ID NO: 1, wherein the altered human telomerase polypeptide comprises at least one amino acid substitution that is at position R19, L22, R132, L152, D444, K492, E555, L556, T564, R572, R577, D637, L675, E727, R742, T765, R811, L840, G847, T874, L940, K981, V997, or P1020.

Described herein, in certain embodiments, is an altered human telomerase polypeptide with at least 90% identity to the sequence set forth in SEQ ID NOs: 28 or 29, wherein the altered human telomerase polypeptide is not identical to SEQ ID NO: 1.

Described herein, in certain embodiments, is a method for treating an individual with cancer the method comprising administering to an individual with cancer a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27.

Described herein, in certain embodiments, is a method for treating an individual with cancer comprising administering to an individual with cancer an altered human telomerase polypeptide with at least 90% identity to the sequence set forth in SEQ ID NO: 1, wherein the altered human telomerase polypeptide comprises at least one amino acid substitution that is at position R19, L22, R132, L152, D444, K492, E555, L556, T564, R572, R577, D637, L675, E727, R742, T765, R811, L840, G847, T874, L940, K981, V997, or P1020.

Described herein, in certain embodiments, is a method for treating an individual with cancer the method comprising administering to the individual with cancer an altered human telomerase polypeptide at least 90% identical to SEQ ID NO: 28 or 29, wherein the altered human telomerase polypeptide is not identical to SEQ ID NO: 1.

Described herein, in certain embodiments, is a method of preparing a cancer treatment the method comprising admixing a polypeptide comprising at least one sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, or SEQ ID NO: 27, and a pharmaceutically acceptable vehicle, carrier, excipient, or combination thereof.

Described herein, in certain embodiments, is a method of preparing a cancer treatment the method comprising admixing a composition comprising an altered human telomerase polypeptide with at least 90% identity to that set forth in SEQ ID NO: 1, comprising at least one amino acid substitution that is at position R19, L22, R132, L152, D444, K492, E555, L556, T564, R572, R577, D637, L675, E727, R742, T765, R811, L840, G847, T874, L940, K981, V997, or P1020, and a pharmaceutically acceptable vehicle, carrier, excipient, or combination thereof.

Described herein, in certain embodiments, is a method of preparing a cancer treatment the method comprising admixing an altered human telomerase polypeptide at least 90% identical to SEQ ID NO: 28 or 29, wherein the altered human telomerase polypeptide is not identical to SEQ ID NO: 1 and a pharmaceutically acceptable vehicle, carrier, excipient, or combination thereof.

Certain Definitions

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by about 10%, 5%, or 1%.

As used herein "antigen" refers to a molecule capable of inducing an adaptive immune response in the host organism.

As used herein "epitope" refers to the part of an antigen, protein, or polypeptide that is recognized by the immune system, specifically by antibodies, B cell receptors, or T cell receptors.

As used herein "immunological adjuvant" refers to any substance that can be administered with an antigen to increase the immune response in response to that antigen.

As used herein "T cell helper epitope" refers to a polypeptide capable of stimulating a CD4$^+$ T cell to secrete immunostimulatory factors (e.g., cytokines, chemokines) and improve the immunogenicity of antigens with regard to B cell, CD4$^+$ T cell and/or cytotoxic CD8$^+$ T cell responses.

Altered Telomerase Polypeptides

In certain embodiments, described herein, are compositions of matter. SEQ ID NO: 1 corresponds to the amino acid sequence of wild type human telomerase protein. In certain embodiments, described herein, the composition is an altered telomerase polypeptide that has been altered from the sequence set forth in SEQ ID NO: 1. In certain embodiments, the polypeptide that has been altered from the sequence set forth in SEQ ID NO: 1, has been altered in a way to increase immunogenicity of one or more T cell epitopes derived therefrom. In certain embodiments, the altered telomerase polypeptide has been altered to correspond to the amino acid sequence set forth in SEQ ID NO: 28 or SEQ ID NO: 29. In certain embodiments, the altered telomerase polypeptide has been altered to possess 90% sequence identity to SEQ ID NO: 28 or SEQ ID NO: 29. In certain embodiments, the altered telomerase polypeptide has been altered to possess 95% sequence identity to SEQ ID NO: 28 or SEQ ID NO: 29. In certain embodiments, the altered telomerase polypeptide has been altered to possess 97% sequence identity to SEQ ID NO: 28 or SEQ ID NO: 29. In certain embodiments, the altered telomerase polypeptide has been altered to possess 98% sequence identity to SEQ ID NO: 28 or SEQ ID NO: 29. In certain embodiments, the altered telomerase polypeptide has been altered to possess 99% sequence identity to SEQ ID NO: 28 or SEQ ID NO: 29. In certain embodiments, the altered telomerase polypeptide has been altered to possess 100% sequence identity to SEQ ID NO: 28 or SEQ ID NO: 29. In certain embodiments, SEQ ID NO: 28 or SEQ ID NO: 29 comprises one or more T cell helper epitopes that have been inserted into the polypeptide sequence of SEQ ID NO: 28 or SEQ ID NO: 29, or at the N or C-terminal ends, possibly joined by a flexible linker. In a further embodiment, the altered telomerase polypeptide may comprise truncations or deletions of amino acid residues that do not interfere with a T cell epitope.

In certain embodiments, described herein, are compositions of matter. In certain embodiments, the composition of matter is an altered telomerase polypeptide of SEQ ID NO: 1, wherein the alteration occurs at any one or more of positions R19, L22, R132, L152, D444, K492, E555, L556, T564, R572, R577, D637, L675, E727, R742, T765, R811, L840, G847, T874, L940, K981, V997, P1020, or any combination thereof. In certain embodiments, the alteration of SEQ ID NO: 1 occurs at any two or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any three or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any four or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any five or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any six or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any seven or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any eight or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any nine or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any ten or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any fifteen or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any twenty or more of positions R19, L22, R132, L152, D444, K492, E555, L556, T564, R572, R577, D637, L675, E727, R742, T765, R811, L840, G847, T874, L940, K981, V997, or P1020. In certain embodiments, the alteration of SEQ ID NO: 1 occurs at any twenty-five or more of positions R19, L22, R132, L152, D444, K492, E555, L556, T564, R572, R577, D637, L675, E727, R742, T765, R811, L840, G847, T874, L940, K981, V997, or P1020. In certain embodiments, the altered telomerase polypeptide retains 90% sequence identity to SEQ ID NO: 1. In certain embodiments, the altered telomerase polypeptide retains 95% sequence identity to SEQ ID NO: 1. In certain embodiments, the altered telomerase polypeptide retains 97% sequence identity to SEQ ID NO: 1. In certain embodiments, the altered telomerase polypeptide retains 98% sequence identity to SEQ ID NO: 1. In certain embodiments, the altered telomerase polypeptide retains 99% sequence identity to SEQ ID NO: 1. In certain embodiments, the altered telomerase polypeptide comprises a T cell helper epitope that has been inserted into the polypeptide sequence. In certain embodiments, the T cell helper epitope is inserted at the N-terminus. In certain embodiments, the T helper epitope is inserted at the C-terminus. In certain embodiments, the T cell helper epitope is inserted in any region of the altered telomerase polypeptide that does not disrupt any T cell epitope listed as SEQ ID NO: 2 to SEQ ID NO: 27. In certain embodiments, the T cell helper epitope is inserted in the altered telomerase polypeptide somewhere between amino acids 140 and 440. In certain embodiments, the T cell helper epitope is inserted in the altered telomerase polypeptide somewhere between amino acids 500 and 550. In certain embodiments, the T cell helper epitope is inserted in the altered telomerase polypeptide somewhere between amino acids 770 and 810. In certain embodiments, the T cell helper epitope comprises a non-human polypeptide derived from a virus, bacteria, or parasite. In certain embodiments, the T cell helper epitope comprises a sequence from the tetanus toxoid protein. In certain embodiments, the T cell helper epitope is set forth SEQ ID NO: 30. In certain embodiments, the composition comprises a T cell helper epitope that is a separate polypeptide from the altered telomerase polypeptide. In a further embodiment, the altered telomerase polypeptide may comprise truncations or deletions of amino acid residues that do not interfere with a T cell epitope.

HLA Binding Properties of Altered Telomerase Peptides

In certain embodiments, amino acid alterations in SEQ ID NO: 1 produce polypeptides that increase binding affinity to an HLA molecule. In certain embodiments, an alteration increases binding of an altered peptide to an HLA molecule by two-fold. In certain embodiments, an alteration increases binding of an altered peptide to an HLA molecule by five-fold. In certain embodiments, an alteration increases binding of an altered peptide to an HLA molecule by ten-fold. In certain embodiments, the HLA molecule is any one or more of types A1, A2, A3, A11, A24, B7 and B44.

In certain embodiments, described herein, are compositions of matter. In certain embodiments, the composition of matter is a polypeptide. In certain embodiments, the polypeptide comprises any one or more amino acid sequence as set forth in SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, SEQ ID NO: 27 (also referred to as SEQ ID NO:2 to SEQ ID NO: 27 for brevity), or any combination thereof. Table 1 shows SEQ ID NO:2 to SEQ ID NO: 27 and the HLA type bound by each. In certain embodiments, the polypeptide comprises any two or more amino acid sequence as set forth in SEQ ID NO:2 to SEQ ID NO: 27. In certain embodiments, the polypeptide comprises any three or more amino acid sequence as set forth in SEQ ID NO:2 to SEQ ID NO: 27. In certain embodiments, the polypeptide comprises any four or more amino acid sequence as set forth in SEQ ID NO:2 to SEQ ID NO: 27. In certain embodiments, the polypeptide comprises any five or more amino acid sequence as set forth in SEQ ID NO:2 to SEQ ID NO: 27. In certain embodiments, the polypeptide comprises any six or more amino acid sequence as set forth in SEQ ID NO:2 to SEQ ID NO: 27. In certain embodiments, the polypeptide comprises any seven or more amino acid sequence as set forth in SEQ ID NO:2 to SEQ ID NO: 27. In certain embodiments, the polypeptide comprises any eight or more amino acid sequence as set forth in SEQ ID NO:2 to SEQ ID NO: 27. In certain embodiments, the polypeptide comprises any nine or more amino acid sequence as set forth in SEQ ID NO:2 to SEQ ID NO: 27. In certain embodiments, the polypeptide comprises any ten or more amino acid sequence as set forth in SEQ ID NO:2 to SEQ ID NO: 27. In certain embodiments, the polypeptide comprises any fifteen or more amino acid sequence as set forth in SEQ ID NO:2 to SEQ ID NO: 27. In certain embodiments, the polypeptide comprises any twenty or more amino acid sequence as set forth in SEQ ID NO:2 to SEQ ID NO: 27. In certain embodiments, the polypeptide comprises any twenty-five or more amino acid sequence as set forth in SEQ ID NO:2 to SEQ ID NO: 27. In certain embodiments, the polypeptide does not comprise SEQ ID NO: 12. In certain embodiments, the polypeptide does not comprise SEQ ID NO: 13.

In certain embodiments, the poly peptide comprises any two or more sequences set forth in SEQ ID NO:2 to SEQ ID NO: 27, further comprising amino acid linkers in between each polypeptide set forth in SEQ ID NO:2 to SEQ ID NO: 27. In certain embodiments, the linker sequence is engineered to promote proper cleave by the cell during processing of the polypeptide. In certain embodiments, the linker is at least five amino acids in length. In certain embodiments, the linker is at least seven amino acids in length. In certain embodiments, the linker is at least ten amino acids in length. In certain embodiments, the polypeptide is at least 20 amino acids in length. In certain embodiments, the polypeptide is at least 30 amino acids in length. In certain embodiments, the polypeptide is at least 40 amino acids in length. In certain embodiments, the polypeptide is at least 50 amino acids in length. In certain embodiments, the polypeptide is at least 100 amino acids in length. In certain embodiments, the polypeptide is at least 150 amino acids in length. In certain embodiments, the polypeptide is at least 200 amino acids in length. In certain embodiments, the polypeptide is less than 500 amino acids in length. In certain embodiments, the polypeptide is less than 400 amino acids in length. In certain embodiments, the polypeptide is less than 300 amino acids in length.

In certain embodiments, the polypeptide comprises at least one amino acid sequence set forth in SEQ ID NO:2 to SEQ ID NO: 27, and a T cell helper epitope. In certain embodiments, the T cell helper epitope is inserted at the N-terminus. In certain embodiments, the T helper epitope is inserted at the C-terminus. In certain embodiments, the T cell helper epitope is inserted in any region of the polypeptide that does not disrupt another T cell epitope set forth in SEQ ID NO: 2 to SEQ ID NO: 27. In certain embodiments, the T cell helper epitope comprises a non-human polypeptide derived from a virus, bacteria, or parasite. In certain embodiments, the T cell helper epitope is set forth in SEQ ID NO: 30 to SEQ ID NO: 55. In certain embodiments, the T cell helper epitope comprises a sequence from the tetanus toxoid protein. In certain embodiments, the T cell helper epitope is set forth in SEQ ID NO: 30. In certain embodiments, the composition comprises a T cell helper epitope that is separate polypeptide from the altered telomerase polypeptide.

In certain embodiments, the polypeptide comprises all polypeptides known to bind a given HLA type. In certain embodiments, the polypeptide comprises A1 binders SEQ ID NO: 19 and SEQ ID NO: 21. In certain embodiments, the polypeptide comprises A2 binders SEQ ID NO: 5, SEQ ID NO: 6, SEQ ID NO: 10, SEQ ID NO: 12, SEQ ID NO: 16, SEQ ID NO: 20, and SEQ ID NO: 25. In certain embodiments, the polypeptide comprises A3 binders SEQ ID NO: 8, SEQ ID NO: 11, SEQ ID NO: 26, and SEQ ID NO: 27. In certain embodiments, the polypeptide comprises A11 binders SEQ ID NO: 8, SEQ ID NO: 17, and SEQ ID NO: 18. In certain embodiments, the polypeptide comprises A24 binders SEQ ID NO: 14, SEQ ID NO: 15, and SEQ ID NO: 24. In certain embodiments, the polypeptide comprises B7 binders SEQ ID NO: 4, SEQ ID NO: 7, and SEQ ID NO: 23. In certain embodiments, the polypeptide comprises B44 binders SEQ ID NO: 2, SEQ ID NO: 9, and SEQ ID NO: 24.

In certain embodiments, the polypeptide comprises at least seven different sequences, wherein each of the seven different sequences binds a different human leukocyte antigen selected from the group consisting of A1, A2, A3, A11, A24, B3, B7 and B44. In certain embodiments, the polypeptide comprises one A1 binder selected from the group consisting of SEQ ID NO: 19 and SEQ ID NO: 21; one A2 binder selected from the group consisting of SEQ ID NO: 5, SEQ ID NO: 6, SEQ ID NO: 10, SEQ ID NO: 12, SEQ ID NO: 16, SEQ ID NO: 20, and SEQ ID NO: 25; one A3 binder selected from the group consisting of SEQ ID NO: 8, SEQ ID NO: 11, SEQ ID NO: 26, and SEQ ID NO: 27; one A11 binder selected from the group consisting of SEQ ID NO: 8, SEQ ID NO: 17, and SEQ ID NO: 18; one A24 binder selected from the group consisting of SEQ ID NO: 14, SEQ ID NO: 15, and SEQ ID NO: 24; one B7 binder selected from the group consisting of SEQ ID NO: 4, SEQ ID NO: 7, and SEQ ID NO: 23; and one B44 binder selected from the group consisting of SEQ ID NO: 2, SEQ ID NO: 9, and SEQ ID NO: 24

TABLE 1

Bold and underline denotes residue altered from wild type human telomerase sequence

| SEQ ID | SEQUENCE | HLA TYPE BOUND |
|---|---|---|
| 2 | AEVLPLATF | B44 |
| 3 | AEVRPLATF | B44 |
| 4 | RPLATFVRRL | B7 |
| 5 | ALMGSGAWGL | A2 |
| 6 | YLARCALFV | A2 |
| 7 | RPRRLVQLL | B7 |
| 8 | NTMKFISLGK | A11 and A3 |
| 9 | VEMLRSFFY | B44 |
| 10 | YLLRSFFYV | A2 |
| 11 | YVYETTFQK | A3 |
| 12 | YLFFYMKSV | A2 |
| 13 | YLFFYRKSV | A2 |
| 14 | FYMKSVWSKL | A24 |
| 15 | YYVVGARTF | A24 |
| 16 | YLGASVLGL | A2 |
| 17 | LTMVIASIIK | A11 |
| 18 | CVMRYAVVQK | A11 |
| 19 | VSDLTDLQPY | A1 |
| 20 | FLMFMCHHAV | A2 |
| 21 | STDLCSLCY | A1 |
| 22 | CYMDMENKLF | A24 |

TABLE 1-continued

Bold and underline denotes residue altered from wild type human telomerase sequence

| SEQ ID | SEQUENCE | HLA TYPE BOUND |
|---|---|---|
| 23 | RPHLTHAKTF | B7 |
| 24 | AEVQSDYSSY | B44 |
| 25 | RLMCHSLFL | A2 |
| 26 | QTYCTNIYK | A3 |
| 27 | QLYFHQQVWK | A3 |

Nucleic Acids

In certain embodiments, described herein, are nucleic acids that encode the polypeptides and altered telomerase polypeptides described herein. In certain embodiments, the nucleic acid is a plasmid. In certain embodiments, the nucleic acid is a viral vector. In certain embodiments, the viral vector is an adenovirus, lentivirus, retrovirus, adeno associated virus, or vaccinia virus. In certain embodiments, the nucleic acid comprises RNA. In certain embodiments, the nucleic acid encodes any of SEQ ID NOs: 2 to 55. In certain embodiments, the nucleic acid encodes any polypeptide embodiment described herein. In certain embodiments, the nucleic acid is expressed via a universal promoter such as the CMV promoter. In certain embodiments, the nucleic acid is expressed via a tissue specific promoter. In certain embodiments, the tissue specific promoter is a B cell specific promoter. In certain embodiments, the tissue specific promoter is the immunoglobulin promoter/enhancer.

T Cell Helper Epitope

In certain embodiments, any of the compositions described herein, comprise a T cell helper epitope. In certain embodiments, any of the polypeptides described herein, comprise a T cell helper epitope. In certain embodiments, any of the treatment methods described herein, comprise administering an altered telomerase polypeptide in conjunction with a T cell helper epitope. In certain embodiments, the T cell helper epitope is a promiscuous binder and binds more than one human MHC Class II HLA type. In certain embodiments, the T cell helper epitope comprises a non-human polypeptide derived from a virus, bacteria, or parasite. In certain embodiments, the T cell helper epitope comprises an artificial sequence. In certain embodiments, the T cell helper epitope comprises a chimeric sequence from a plurality of antigens. In certain embodiments, the T cell helper epitope comprises any of the SEQ IDs listed in Table 2. In certain embodiments, the T cell helper epitope comprises any of SEQ ID NO:30 to SEQ ID NO: 55. In certain embodiments, the T cell helper epitope comprises a sequence from the tetanus toxoid protein. In certain embodiments, the T cell helper epitope is set forth in SEQ ID NO: 30. In certain embodiments, the T cell helper epitope is inserted into telomerase in such a way a to destroy the telomerase activity.

TABLE 2

| SEQ ID | SEQUENCE | SOURCE |
|---|---|---|
| 30 | QYIKANSKFIGITE | Tetanus Toxoid |
| 31 | AKFVAAWTLKAAA | Artificial |

TABLE 2-continued

| SEQ ID | SEQUENCE | SOURCE |
|---|---|---|
| 32 | EKKIAKMEKASSVFNVVNS | Malaria |
| 33 | IEKKIAKMEKASSVFNVVNS | Malaria |
| 34 | DIEKKIAKMEKASSVFNVVNS | Malaria |
| 35 | DIEKKIAKMEKASSVFNVVN | Malaria |
| 36 | DIEKKIAKMEKASSVFNVV | Malaria |
| 37 | DIEKKIAKMEKASSVFNV | Malaria |
| 38 | ILMQYIKANSKFIGI | Chimeric-tetanus toxoid; diphtheria toxoid |
| 39 | QSIALSSLMVAQAIP | Chimeric-tetanus toxoid; diphtheria toxoid |
| 40 | ILMQYIKANSKFIGIPMGLPQSIALSSLMVAQ | Chimeric-tetanus toxoid; diphtheria toxoid |
| 41 | ILMQYIKANSKFIGIKVSRQSIALSSLMVAQ | Chimeric-tetanus toxoid; diphtheria toxoid |
| 42 | KVLVLNPSVAATLGF | Hepatitis C virus |
| 43 | PTHFKYHEKHYYNAQ | BK Virus |
| 44 | LFVVYRDSIPHAACH | Human papilloma virus |
| 45 | GLYNLLIRCLRCQKP | Human papilloma virus |
| 46 | GKTVWFVPSIKAGND | Dengue virus |
| 47 | MYFHRRDLRLASNAI | Dengue virus |
| 48 | VERLKRMAISGDDCVVK | Dengue virus |
| 49 | ANAIFKLTYQNKVVKVQ | Dengue virus |
| 50 | ASIAARGYISTRVGM | Dengue virus |
| 51 | DENPYKTWAYHGSYEVK | Dengue virus |
| 52 | EAAAIFMTATPPGTA | Dengue virus |
| 53 | MVTQMAMTDTTPFGQQR | Dengue virus |
| 54 | KKRNLTIMDLHPGSG | Dengue virus |
| 55 | LSEJKGVIVHRLEGV | Measles virus |

Antigen Presenting Cells

In certain embodiments, described herein, telomerase polypeptides, form a complex with HLA molecules on the surface of antigen presenting cells. In certain embodiments, the polypeptide comprises a SEQ ID set forth in SEQ ID NOs:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO: 25, SEQ ID NO: 26, SEQ ID NO: 27, or any combination thereof. In certain embodiments, described herein, 8-10 contiguous amino acids derived from an altered telomerase polypeptide by cellular processing, form a complex with one or more HLA molecules on the surface of antigen presenting cell. In certain embodiments, the antigen presenting cell encounters the telomerase polypeptide in vivo after the polypeptide has been administered to an individual. In certain embodiments, the polypeptide is added to antigen presenting cells ex vivo. In certain embodiments, the antigen presenting cell has been treated ex vivo to activate its antigen presenting capacity. In certain embodiments, the antigen presenting cell has been treated with interferon gamma, granulocyte-macrophage colony-stimulating factor (GM-CSF), colony-stimulating factor, a TLR ligand, lipopolysaccharide, CpG oligonucleotide, or any combination thereof. In certain embodiments, the antigen presenting cell comprises a B cell. In certain embodiments, the antigen presenting cell comprises a dendritic cell. In certain embodiments, the antigen presenting cell comprises a macrophage. In certain embodiments, the antigen presenting cell comprises an artificial antigen presenting cell.

Immunological Adjuvants

In certain embodiments, described herein, are compositions of matter that comprise an altered telomerase polypeptide and an immunological adjuvant. In certain embodiments, described herein, are compositions of matter that comprise any of SEQ ID NOs: 2 to 29 and an immunological adjuvant. In certain embodiments, the adjuvant comprises an adjuvant currently used in vaccination. In certain embodiments, the adjuvant is mineral salt. In certain embodiments, the adjuvant comprises alum salt. In certain embodiments, the adjuvant comprises aluminum phosphate or aluminum hydroxide. In certain embodiments, the adjuvant comprises Quil A or saponin QS-21. In certain embodiments, the adjuvant comprises N-acetyl muramyl-L-alanyl-D-isoglutamine, also called MDP. In certain embodiments, the adjuvant comprises IFA, Montanide, Adjuvant 65, and Lipovant. In certain embodiments, the adjuvant comprises a cytokine such as interferon gamma or GM-CSF.

Toll-Like Receptor Ligands

In certain embodiments, described herein, are compositions of matter that comprise an altered telomerase polypeptide and a Toll-like receptor (TLR) ligand, a STING agonist, or RIG-I agonist. In certain embodiments, described herein, are compositions of matter that comprise any of SEQ ID NOs: 2 to 29 and a TLR ligand. In certain embodiments, the TLR ligand is LPS or a CpG oligonucleotide. In certain embodiments, the TLR ligand activates signaling through any one of TLR2, TLR3, TLR4, TLR5, TLR6, TLR7, TLR8, or TLR9. In certain embodiments, the STING agonist comprises a cyclic dinucleotide. In certain embodiments, the RIG-1 agonist comprises a 5'ppp-dsRNA.

Pharmaceutically Acceptable Vehicles, Carrier and Excipients

In certain embodiments, described herein, are compositions of matter that comprise an altered telomerase polypeptide and a pharmaceutically acceptable vehicle, carrier, or excipient. In certain embodiments, described herein, are compositions of matter that comprise any of SEQ ID NOs: 2 to 29 and a pharmaceutically acceptable vehicle, carrier or excipient. In certain embodiments, the pharmaceutically acceptable vehicle, carrier, or excipient comprises a pH buffer or pH modifier. In certain embodiments, the pH buffer or pH modifier comprises sodium bicarbonate, HEPES, MOPS, MEPES, phosphate buffer, succinate buffer, citric acid, ascorbic acid, or any combination thereof. In certain embodiments, the pharmaceutically acceptable vehicle, carrier or excipient comprises a salt solution. In certain embodiments, the salt solution comprises sodium chloride, potassium chloride, calcium chloride, hemin chloride, benzethonium chloride, or any combination thereof. In certain embodiments, the pharmaceutically acceptable vehicle, carrier or excipient comprises a carbohydrate. In certain embodiments, the carbohydrate comprises sucrose, dextrose, trehalose, lactose, cellulose, sorbitol, galactose, dextran, xanthan, or any combination thereof. In certain embodiments, the pharmaceutically acceptable vehicle, carrier or excipient comprises an amino acid or protein. In certain embodiments, the amino acid or protein comprises gelatin, egg protein, yeast extract, glutamate, albumin, In certain embodiments, the pharmaceutically acceptable vehicle, carrier or excipient comprises an emulsifier. In certain embodiments, the emulsifier comprises octylphenol ethoxylate (Triton X-100), polysorbate 20, polysorbate 80 (Tween 80), sodium deoxy cholate, or any combination thereof. In certain embodiments, the pharmaceutically acceptable vehicle, carrier or excipient comprises a chelator. In certain embodiments, the chelator comprises ethylene diamine tetra acetic acid sodium (EDTA), EGTA, or any combination thereof. In certain embodiments, the pharmaceutically acceptable vehicle, carrier or excipient comprises a liposome. In certain embodiments, the liposome comprises a phospholipid, such as, for example, phosphatidylcholine. The liposome can be multilamellar or unilamellar.

Routes of Administration

In certain embodiments, the polypeptides and nucleic acids of the current disclosure can be administered in a variety of ways. In certain embodiments, the polypeptides are delivered via a subcutaneous or intradermal injection. In certain embodiments, the polypeptides can be administered by electroporation. In certain embodiments, the polypeptides are delivered via an intra-tumor injection. In certain embodiments, the polypeptides are delivered via injection to the spleen or lymph nodes. In certain embodiments, the polypeptides are delivered bound to the HLA of an antigen presenting cell by intravenous administration. In certain embodiments, the antigen presenting cell is a B cell. In certain embodiments, the antigen presenting cell is a dendritic cell. In certain embodiments, the nucleic acids of the current disclosure can be administered by transfection. In certain embodiments, the nucleic acids of the current disclosure can be administered by electroporation. In certain embodiments, the nucleic acids of the current disclosure can be administered by transfection of an antigen presenting cell ex vivo. In certain embodiments, the antigen presenting cell is a B cell. In certain embodiments, the antigen presenting cell is a dendritic cell. In certain embodiments, the altered telomerase polypeptides can be used in conjunction with chimeric antigen receptor (CAR) T cells or NK cells. In certain embodiments, the CAR-T cells are specific for a telomerase peptide set forth is SE ID NO:2 to SEQ ID NO: 27. In certain embodiments, the CAR-NK cells are specific for a telomerase peptide set forth is SE ID NO:2 to SEQ ID NO: 27.

In certain embodiments, antigen presenting cells are isolated from an individual with cancer, the antigen presenting cell is transfected ex vivo with a nucleic acid encoding any of the altered telomerase polypeptides of the present disclosure, and then administered to the individual. In certain embodiments, the antigen presenting cell is transfected by a lipid transfection reagent. In certain embodiments, the antigen presenting cell is transfected by electroporation. In certain embodiments, the antigen presenting cell is transfected by a viral vector. In certain embodiments, the antigen presenting cell is transfected spontaneously without the aid of a specific transfection reagent. In certain embodiments, the antigen presenting cell comprises a B cell. In certain embodiments, the antigen presenting cell comprises a dendritic cell. In certain embodiments, the antigen presenting cell comprises a macrophage. In certain embodiments, $1 \times 10^5$ to $5 \times 10^6$ of the transfected antigen presenting cells are administered to an individual. In certain embodiments, at least $1 \times 10^5$ of the transfected antigen presenting cells are administered to an individual. In certain embodiments, at least $1 \times 10^6$ of the transfected antigen presenting cells are administered to an individual.

Schedules and Method of Administration

In certain embodiments, described herein, are methods of treating cancer using the polypeptides or nucleotides of the present disclosure. In certain embodiments, any of the polypeptides or nucleotides are administered once to an individual in need. In certain embodiments, any of the polypeptides or nucleotides are administered twice to an individual in need. In certain embodiments, any of the polypeptides or nucleotides are administered three times to an individual in need. In certain embodiments, any of the polypeptides or nucleotides are administered four times or more to an individual in need. In certain embodiments, individuals are primed with one polypeptide and boosted with the same polypeptide. In certain embodiments, individuals are primed with one polypeptide and boosted with a different polypeptide. In certain embodiments, individuals are primed with a nucleic acid and boosted with a polypeptide. In certain embodiments, doses are given once a week, once every two weeks, once a month, or once a year. In certain embodiments, the interval between doses is at least one month. In certain embodiments, the interval between doses is at least two months. In certain embodiments, individuals who have responded to the treatment are given annual or semi-annual booster doses.

Method of Preparation of a Cancer Treatment

In certain embodiments, described herein, are methods of producing polypeptides comprising SEQ ID NO:2 to SEQ ID NO: 27, and altered telomerase polypeptides. In certain embodiments, are methods that comprise preparing any of SEQ ID NOs: 2 to 55. The polypeptides of this disclosure can be produced by techniques know in the art. In certain embodiments, the polypeptides are synthesized. In certain embodiments, the polypeptides are expressed in a suitable expression system and purified using standard techniques such as filtration, precipitation, chromatography, centrifugation, or any combination thereof.

Cancers

In certain embodiments, the compositions and methods described herein, are for use in treating an individual with cancer. In certain embodiments, the individual has any stage of histologically confirmed cancer. In certain embodiments, the individual is at risk of developing cancer. In certain embodiments, the cancer is telomerase positive. In certain embodiments, the cancer is any cancer that has been shown to have telomerase activity or elevated levels of telomerase. Elevated levels of telomerase activity can be shown by TRAP assay, or elevations in telomerase mRNA or protein levels. In certain embodiments, the cancer is caused by a mutation in the telomerase promoter region. In certain embodiments, the cancer is associated with a mutation in the telomerase promoter region. In certain embodiments, the cancer is a solid tumor. In certain embodiments, the cancer is hematological. In certain embodiments, the cancer is a brain cancer. In certain embodiments, the brain cancer is a glioblastoma. In certain embodiments, the cancer is a liver cancer. In certain embodiments, the liver cancer is hepatocellular carcinoma. In certain embodiments, the cancer is of the urogenital system. In certain embodiments, the urogenital system cancer is bladder cancer. In certain embodiments, the urogenital system cancer is prostate cancer. In certain embodiments, the cancer is kidney cancer. In certain embodiments, the cancer is thyroid cancer. In certain embodiments, the cancer is prostate cancer, breast cancer, colon cancer, pancreatic cancer, melanoma, lung cancer, stomach cancer, or brain cancer. In certain embodiments, the cancer is a blood cancer such as a leukemia or myeloma. In certain embodiments, the blood cancer is chronic myelogenous leukemia, acute myelogenous leukemia, chronic lymphocytic leukemia, acute lymphocytic leukemia, or multiple myeloma.

EXAMPLES

The following examples are meant to be illustrative and do not serve to limit the invention described herein.

Example 1—A Clinical Trial for Bladder Cancer Using B Cells Transfected with Plasmid Expressing an Altered Telomerase Polypeptide A clinical trial will be conducted for patients with a telomerase specific cancer such as bladder/urothelial cancer. The primary efficacy endpoint will be the percentage survivorship 24 months post treatment. The treatment will be with a B cell population transfected with a nucleic acid plasmid encoding an altered telomerase corresponding to SEQ ID NO: 28 or 29. Peripheral blood mononuclear cells will be isolated from each patient, spontaneously transfected ex vivo with plasmid DNA, and cultured for 24 hours under cell type appropriate culture conditions. After this culture period patients will be injected intravenously with $1 \times 10^5$ to $5 \times 10^6$ of their own B cells in an autologous transfer. Patients will be administered a total of three treatments 1 month apart.

Example 2—Immunization of Patients with Melanoma Using an Altered Telomerase Polypeptide One mg of an altered telomerase polypeptide will be administered subcutaneously or intradermally to patients with melanoma. The altered telomerase polypeptide will be prepared with an immunological adjuvant. Patients will be administered a total of three treatments one month apart.

Example 3—Immunization of Patients with Hepatocellular Carcinoma Using Plasmid DNA in Conjunction with Electroporation 100 micrograms of a plasmid encoding an altered telomerase peptide will be administered intradermally at ten different sites on the patient using electroporation. A total of one milligram will be administered.

Example 4—Delivering a Booster Dose Via a Viral Vector

A booster dosage of a viral vector will be administered to a person previously immunized with nucleic acid or peptide. The viral vector will encode a polypeptide corresponding to SEQ ID NO: 28 or SEQ ID NO: 29 or any other polypeptide disclosed herein. The booster will occur at least one month after the initial immunization.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

```
Wild type human telomerase
                                              SEQ ID NO: 1
         10         20         30         40         50
    MPRAPRCRAV RSLLRSHYRE VLPLATFVRR LGPQGWRLVQ RGDPAAFRAL 60         70         80         90         100
    VAQCLVCVPW DARPPPAAPS FRQVSCLKEL VARVLQRLCE RGAKNVLAFG
```

-continued

```
          110        120        130        140        150
FALLDGARGG PPEAFTTSVR SYLPNTVTDA LRGSGAWGLL LRRVGDDVLV 160        170        180        190        200
HLLARCALFV LVAPSCAYQV CGPPLYQLGA ATQARPPPHA SGPRRRLGCE 210        220        230        240        250
RAWNHSVREA GVPLGLPAPG ARRGGSASR  SLPLPKRPRR GAAPEPERTP 260        270        280        290        350
VGQGSWAHPG RTRGPSDRGF CVVSPARPAE EATSLEGALS GTRHSHPSVG 310        320        330        340        350
RQHHAGPPST SRPPRPWDTP CPPVYAETKH FLYSSGDKEQ LRPSFLLSSL 360        370        380        390        400
RPSLTGARRL VETIFLGSRP WMPGTPRRLP RLPQRYWQMR PLFLELLGNH 410        420        430        440        450
AQCPYGVLLK THCPLRAAVT PAAGVCAREK PQGSVAAPEE EDTDPRRLVQ 460        470        480        490        500
LLRQHSSPWQ VYGFVRACLR RLVPPGLWGS RHNERRFLRN TKKFISLGKH 510        520        530        540        550
AKLSLQELTW KMSVRDCAWL RRSPGVGCVP AAEHRLREEI LAKFLHWLMS 560        570        580        590        600
VYVVELLRSF FYVTETTFQK NRLFFYRKSV WSKLQSIGIR QHLKRVQLRE 610        620        630        640        650
LSEAEVRQHR EARPALLTSR LRFIPKPDGL RPIVNMDYVV GARTFRREKR 660        670        680        690        700
AERLTSRVKA LFSVLNYERA RRPGLLGASV LGLDDIHRAW RTFVLRVRAQ 710        720        730        740        750
DPPPELYFVK VDVTGAYDTI PQDRLTEVIA SIIKPQNTYC VRRYAVVQKA 760        770        780        790        800
AHGHVRKAFK SHVSTLTDLQ PYMRQFVAHL QETSPLRDAV VIEQSSSLNE 810        820        830        840        850
ASSGLFDVFL RFMCHHAVRI RGKSYVQCQG IPQGSILSTL LCSLCYGDME 860        870        880        890        900
NKLFAGIRRD GLLLRLVDDF LLVTPHLTHA KTFLRTLVRG VPEYGCVVNL 910        920        930        940        950
RKTVVNFPVE DEALGGTAFV QMPAHGLFPW CGLLLDTRTL EVQSDYSSYA 960        970        980         90       1000
RTSIRASLTF NRGFKAGRNM RRKLFGVLRL KCHSLFLDLQ VNSLQTVCTN 1010       1020       1030       1040       1050
IYKILLLQAY RFHACVLQLP FHQQVWKNPT FFLRVISDTA SLCYSILKAK 1060       1070       1080       1090       1100
NAGMSLGAKG AAGPLPSEAV QWLCHQAFLL KLTRHRVTYV PLLGSLRTAQ 1110        112       1130
TQLSRKLPGT TLTALEAAAN PALPSDFKTI LD

Altered human telomerase variant 1
                                                     SEQ ID NO: 28
           10         20         30         40         50
MPRAPRCRAV RSLLRSHYAE VRPLATFVRR LGPQGWRLVQ RGDPAAFRAL 60         70         80         90        100
VAQCLVCVPW DARPPPAAPS FRQVSCLKEL VARVLQRLCE RGAKNVLAFG 110        120        130        140        150
FALLDGARGG PPEAFTTSVR SYLPNTVTDA LMGSGAWGLL LRRVGDDVLV 160        170        180        190        200
HLLARCALFV LVAPSCAYQV CGPPLYQLGA ATQARPPPHA SGPRRRLGCE 210        220        230        240        250
RAWNHSVREA GVPLGLPAPG ARRGGSASR  SLPLPKRPRR GAAPEPERTP
```

```
              260        270        280        290        350
       VGQGSWAHPG RTRGPSDRGF CVVSPARPAE EATSLEGALS GTRHSHPSVG 310        320        330        340        350
       RQHHAGPPST SRPPRPWDTP CPPVYAETKH FLYSSGDKEQ LRPSFLLSSL 360        370        380        390        400
       RPSLTGARRL VETIFLGSRP WMPGTPRRLP RLPQRYWQMR PLFLELLGNH 410        420        430        440        450
       AQCPYGVLLK THCPLRAAVT PAAGVCAREK PQGSVAAPEE EDTRPRRLVQ 460        470        480        490        500
       LLRQHSSPWQ VYGFVRACLR RLVPPGLWGS RHNERRFLRN TMKFISLGKH 510        520        530        540        550
       AKLSLQELTW KMSVRDCAWL RRSPGVGCVP AAEHRLREEI LAKFLHWLMS 560        570        580        590        600
       VYVVEMLRSF FYVYETTFQK NYLFFYMKSV WSKLQSIGIR QHLKRVQLRE 610        620        630        640        650
       LSEAEVRQHR EARPALLTSR LRFIPKPDGL RPIVNMYYVV GARTFRREKR 660        670        680        690        700
       AERLTSRVKA LFSVLNYERA RRPGYLGASV LGLDDIHRAW RTFVLRVRAQ 710        720        730        740        750
       DPPPELYFVK VDVTGAYDTI PQDRLTMVIA SIIKPQNTYC VMRYAVVQKA 760        770        780        790        800
       AHGHVRKAFK SHVSDLTDLQ PYMRQFVAHL QETSPLRDAV VIEQSSSLNE 810        820        830        840        850
       ASSGLFDVFL MFMCHHAVRI RGKSYVQCQG IPQGSILSTD LCSLCYMDME 860        870        880        890        900
       NKLFAGIRRD GLLLRLQYIK ANSKEFIGITE LFLLVRPHLT HAKTFLRTLV 910        920        930        940        950
       RGVPEYGCVV NLRKTVVNFP VEDEALGGTA FVQMPAHGLF PWCGLLLDTR 960        970        980        990       1000
       TAEVQSDYSS YARTSIRASL TFNRGFKAGR NMRRKLFGVL RLMCHSLFLD 1010       1020       1030       1040       1050
       LQVNSLQTYC TNIYKILLLQ AYRFHACVLQ LYFHQQVWKN PTFFLRVISD 1060       1070       1080       1090       1100
       TASLCYSILK AKNAGMSLGA KGAAGPLPSE AVQWLCHQAF LLKLTRHRVT 1110        112       1130       1140
       YVPLLGSLRT AQTQLSRKLP GTTLTALEAA ANPALPSDFK TILD

Altered human telomerase variant 2
                                            SEQ ID NO: 29

10         20         30         40         50
       MPRAPRCRAV RSLLRSHYAE VRPLATFVRR LGPQGWRLVQ RGDPAAFRAL 60         70         80         90        100
       VAQCLVCVPW DARPPPAAPS FRQVSCLKEL VARVLQRLCE RGAKNVLAFG 110        120        130        140        150
       FALLDGARGG PPEAFTTSVR SYLPNTVTDA LMGSGAWGLL LRRVGDDVLV 160        170        180        190        200
       HLLARCALFV LVAPSCAYQV CGPPLYQLGA ATQARPPPHA SGPRRRLGCE 210        220        230        240        250
       RAWNHSVREA GVPLGLPAPG ARRGGSASR SLPLPKRPRR GAAPEPERTP 260        270        280        290        350
       VGQGSWAHPG RTRGPSDRGF CVVSPARPAE EATSLEGALS GTRHSHPSVG 310        320        330        340        350
       RQHHAGPPST SRPPRPWDTP CPPVYAETKH FLYSSGDKEQ LRPSFLLSSL 360        370        380        390        400
       RPSLTGARRL VETIFLGSRP WMPGTPRRLP RLPQRYWQMR PLFLELLGNH
```

-continued

```
          410        420        430        440        450
AQCPYGVLLK THCPLRAAVT PAAGVCAREK PQGSVAAPEE EDTRPRRLVQ 460        470        480        490        500
LLRQHSSPWQ VYGFVRACLR RLVPPGLWGS RHNERRFLRN TMKFISLGKH 510        520        530        540        550
AKLSLQELTW KMSVRDCAWL RRSPGVGCVP AAEHRLREEI LAKFLHWLMS 560        570        580        590        600
VYVVYLLRSF FYVYETTFQK NYLFFYMKSV WSKLQSIGIR QHLKRVQLRE 610        620        630        640        650
LSEAEVRQHR EARPALLTSR LRFIPKPDGL RPIVNMYYVV GARTFRREKR 660        670        680        690        700
AERLTSRVKA LFSVLNYERA RRPGYLGASV LGLDDIHRAW RTFVLRVRAQ 710        720        730        740        750
DPPPELYFVK VDVTGAYDTI PQDRLTMVIA SIIKPQNTYC VMRYAVVQKA 760        770        780        790        800
AHGHVRKAFK SHVSDLTDLQ PYMRQFVAHL QETSPLRDAV VIEQSSSLNE 810        820        830        840        850
ASSGLFDVFL MFMCHHAVRI RGKSYVQCQG IPQGSILSTD LCSLCYMDME 860        870        880        890        900
NKLFAGIRRD GLLLRLQYIK ANSKEFIGITE LFLLVRPHLT HAKTFLRTLV 910        920        930        940        950
RGVPEYGCVV NLRKTVVNFP VEDEALGGTA FVQMPAHGLF PWCGLLLDTR 960        970        980        990       1000
TAEVQSDYSS YARTSIRASL TFNRGFKAGR NMRRKLFGVL RLMCHSLFLD 1010       1020       1030       1040       1050
LQVNSLQTYC TNIYKILLLQ AYRFHACVLQ LYFHQQVWKN PTFFLRVISD 1060       1070       1080       1090       1100
TASLCYSILK AKNAGMSLGA KGAAGPLP    SEAVQWLCHQAF LLKLTRHRVT 1110        112       1130       1140
YVPLLGSLRT AQTQLSRKLP GTTLTALEAA ANPALPSDFK TILD
```

---

What is claimed is:

1. An altered human telomerase polypeptide with at least 90% identity to the sequence set forth in SEQ ID NO: 1, wherein the altered human telomerase polypeptide comprises at least five or more amino acid substitutions that are at position R19, L22, R132, L152, D444, K492, E555, L556, T564, R572, R577, D637, L675, E727, R742, T765, R811, L840, G847, T874, L940, K981, V997, or P1020 of telomerase.

2. The altered human telomerase polypeptide of claim 1, wherein the altered human telomerase polypeptide comprises an insertion of a non-human T cell helper epitope into the polypeptide sequence of the altered human telomerase, wherein the non-human T cell helper epitope binds more than one human class II HLA type.

3. The polypeptide of claim 1 encoded by a polynucleotide.

4. The altered human telomerase polynucleotide of claim 3, wherein the polynucleotide comprises ribonucleic acid (RNA).

5. The altered human telomerase polypeptide of claim 1, wherein at least eight contiguous amino acids of the polypeptide is bound to a cell surface human leukocyte antigen of an antigen presenting cell, wherein the at least eight contiguous amino acids comprise an amino acid substitution of claim 1.

6. The altered human telomerase polypeptide of claim 1, further comprising an immunological adjuvant.

7. The altered human telomerase polypeptide of claim 1, wherein the polypeptide comprises at least 95% identity to the sequence set forth in SEQ ID NO: 1.

8. The altered human telomerase polypeptide of claim 1, wherein the polypeptide comprises at least 98% identity to the sequence set forth in SEQ ID NO: 1.

9. The altered human telomerase polypeptide of claim 2, wherein the non-human T cell helper epitope comprises any one of SEQ ID NO: 30 to SEQ ID NO: 55.

10. The altered human telomerase polypeptide of claim 2, wherein the non-human T cell helper epitope comprises SEQ ID NO: 30.

11. The altered human telomerase polynucleotide of claim 3, wherein the polynucleotide comprises deoxyribonucleic acid (DNA).

* * * * *

SEQUENCE LISTING

<160> NUMBER OF SEQ ID NOS: 56

<210> SEQ ID NO 1
<211> LENGTH: 1132
<212> TYPE: PRT
<213> ORGANISM: Homo sapiens

<400> SEQUENCE: 1

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
                100                 105                 110

```
Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Arg Arg Val
130                 135                 140

Gly Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg
            210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
275                 280                 285

Leu Ser Gly Thr Arg His Ser His Pro Ser Val Gly Arg Gln His His
            290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
            370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525
```

```
Val Pro Ala Ala Glu His Arg Leu Arg Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940
```

-continued

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 2
<211> LENGTH: 9
<212> TYPE: PRT
<213> ORGANISM: Homo sapiens

<400> SEQUENCE: 2

Ala Glu Val Leu Pro Leu Ala Thr Phe
1               5

<210> SEQ ID NO 3
<211> LENGTH: 9
<212> TYPE: PRT
<213> ORGANISM: Homo sapiens

<400> SEQUENCE: 3

Ala Glu Val Arg Pro Leu Ala Thr Phe
1               5

<210> SEQ ID NO 4
<211> LENGTH: 10
<212> TYPE: PRT
<213> ORGANISM: Homo sapiens

<400> SEQUENCE: 4

Arg Pro Leu Ala Thr Phe Val Arg Arg Leu
1               5                   10

<210> SEQ ID NO 5
<211> LENGTH: 10
<212> TYPE: PRT
<213> ORGANISM: Homo sapiens

```
<400> SEQUENCE: 5

Ala Leu Met Gly Ser Gly Ala Trp Gly Leu
1               5                   10

<210> SEQ ID NO 6
<211> LENGTH: 9
<212> TYPE: PRT
<213> ORGANISM: Homo sapiens

<400> SEQUENCE: 6

Tyr Leu Ala Arg Cys Ala Leu Phe Val
1               5

<210> SEQ ID NO 7
<211> LENGTH: 9
<212> TYPE: PRT
<213> ORGANISM: Homo sapiens

<400> SEQUENCE: 7

Arg Pro Arg Arg Leu Val Gln Leu Leu
1               5

<210> SEQ ID NO 8
<211> LENGTH: 10
<212> TYPE: PRT
<213> ORGANISM: Homo sapiens

<400> SEQUENCE: 8

Asn Thr Met Lys Phe Ile Ser Leu Gly Lys
1               5                   10

<210> SEQ ID NO 9
<211> LENGTH: 9
<212> TYPE: PRT
<213> ORGANISM: Homo sapiens

<400> SEQUENCE: 9

Val Glu Met Leu Arg Ser Phe Phe Tyr
1               5

<210> SEQ ID NO 10
<211> LENGTH: 9
<212> TYPE: PRT
<213> ORGANISM: Homo sapiens

<400> SEQUENCE: 10

Tyr Leu Leu Arg Ser Phe Phe Tyr Val
1               5

<210> SEQ ID NO 11
<211> LENGTH: 9
<212> TYPE: PRT
<213> ORGANISM: Homo sapiens

<400> SEQUENCE: 11

Tyr Val Tyr Glu Thr Thr Phe Gln Lys
1               5

<210> SEQ ID NO 12
<211> LENGTH: 9
<212> TYPE: PRT
<213> ORGANISM: Homo sapiens
```

```
<400> SEQUENCE: 12

Tyr Leu Phe Phe Tyr Met Lys Ser Val
1               5

<210> SEQ ID NO 13
<211> LENGTH: 9
<212> TYPE: PRT
<213> ORGANISM: Homo sapiens

<400> SEQUENCE: 13

Tyr Leu Phe Phe Tyr Arg Lys Ser Val
1               5

<210> SEQ ID NO 14
<211> LENGTH: 10
<212> TYPE: PRT
<213> ORGANISM: Homo sapiens

<400> SEQUENCE: 14

Phe Tyr Met Lys Ser Val Trp Ser Lys Leu
1               5                   10

<210> SEQ ID NO 15
<211> LENGTH: 9
<212> TYPE: PRT
<213> ORGANISM: Homo sapiens

<400> SEQUENCE: 15

Tyr Tyr Val Val Gly Ala Arg Thr Phe
1               5

<210> SEQ ID NO 16
<211> LENGTH: 9
<212> TYPE: PRT
<213> ORGANISM: Homo sapiens

<400> SEQUENCE: 16

Tyr Leu Gly Ala Ser Val Leu Gly Leu
1               5

<210> SEQ ID NO 17
<211> LENGTH: 10
<212> TYPE: PRT
<213> ORGANISM: Homo sapiens

<400> SEQUENCE: 17

Leu Thr Met Val Ile Ala Ser Ile Ile Lys
1               5                   10

<210> SEQ ID NO 18
<211> LENGTH: 10
<212> TYPE: PRT
<213> ORGANISM: Homo sapiens

<400> SEQUENCE: 18

Cys Val Met Arg Tyr Ala Val Val Gln Lys
1               5                   10

<210> SEQ ID NO 19
<211> LENGTH: 10
<212> TYPE: PRT
<213> ORGANISM: Homo sapiens
```

```
<400> SEQUENCE: 19

Val Ser Asp Leu Thr Asp Leu Gln Pro Tyr
1               5                   10

<210> SEQ ID NO 20
<211> LENGTH: 10
<212> TYPE: PRT
<213> ORGANISM: Homo sapiens

<400> SEQUENCE: 20

Phe Leu Met Phe Met Cys His His Ala Val
1               5                   10

<210> SEQ ID NO 21
<211> LENGTH: 9
<212> TYPE: PRT
<213> ORGANISM: Homo sapiens

<400> SEQUENCE: 21

Ser Thr Asp Leu Cys Ser Leu Cys Tyr
1               5

<210> SEQ ID NO 22
<211> LENGTH: 10
<212> TYPE: PRT
<213> ORGANISM: Homo sapiens

<400> SEQUENCE: 22

Cys Tyr Met Asp Met Glu Asn Lys Leu Phe
1               5                   10

<210> SEQ ID NO 23
<211> LENGTH: 10
<212> TYPE: PRT
<213> ORGANISM: Homo sapiens

<400> SEQUENCE: 23

Arg Pro His Leu Thr His Ala Lys Thr Phe
1               5                   10

<210> SEQ ID NO 24
<211> LENGTH: 10
<212> TYPE: PRT
<213> ORGANISM: Homo sapiens

<400> SEQUENCE: 24

Ala Glu Val Gln Ser Asp Tyr Ser Ser Tyr
1               5                   10

<210> SEQ ID NO 25
<211> LENGTH: 9
<212> TYPE: PRT
<213> ORGANISM: Homo sapiens

<400> SEQUENCE: 25

Arg Leu Met Cys His Ser Leu Phe Leu
1               5

<210> SEQ ID NO 26
<211> LENGTH: 9
<212> TYPE: PRT
<213> ORGANISM: Homo sapiens
```

<400> SEQUENCE: 26

Gln Thr Tyr Cys Thr Asn Ile Tyr Lys
1               5

<210> SEQ ID NO 27
<211> LENGTH: 10
<212> TYPE: PRT
<213> ORGANISM: Homo sapiens

<400> SEQUENCE: 27

Gln Leu Tyr Phe His Gln Gln Val Trp Lys
1               5                   10

<210> SEQ ID NO 28
<211> LENGTH: 1145
<212> TYPE: PRT
<213> ORGANISM: Homo sapiens

<400> SEQUENCE: 28

Met Pro Arg Ala Pro Arg Cys Arg Ala Val Arg Ser Leu Leu Arg Ser
1               5                   10                  15

His Tyr Ala Glu Val Arg Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Met Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

```
Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Arg Pro Arg Arg Leu
        435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Met Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Met Leu Arg Ser Phe
545                 550                 555                 560

Phe Tyr Val Tyr Glu Thr Thr Phe Gln Lys Asn Tyr Leu Phe Phe Tyr
                565                 570                 575

Met Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Tyr Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Tyr Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
690                 695                 700
```

```
Glu Leu Tyr Phe Val Lys Val Asp Val Thr Gly Ala Tyr Asp Thr Ile
705                 710                 715                 720

Pro Gln Asp Arg Leu Thr Met Val Ile Ala Ser Ile Ile Lys Pro Gln
            725                 730                 735

Asn Thr Tyr Cys Val Met Arg Tyr Ala Val Val Gln Lys Ala Ala His
                740                 745                 750

Gly His Val Arg Lys Ala Phe Lys Ser His Val Ser Asp Leu Thr Asp
            755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Leu Asn Glu
785                 790                 795                 800

Ala Ser Ser Gly Leu Phe Asp Val Phe Leu Met Phe Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Asp Leu Cys Ser Leu Cys Tyr Met Asp
            835                 840                 845

Met Glu Asn Lys Leu Phe Ala Gly Ile Arg Arg Asp Gly Leu Leu Leu
850                 855                 860

Arg Leu Gln Tyr Ile Lys Ala Asn Ser Lys Glu Phe Ile Gly Ile Thr
865                 870                 875                 880

Glu Leu Phe Leu Leu Val Arg Pro His Leu Thr His Ala Lys Thr Phe
                885                 890                 895

Leu Arg Thr Leu Val Arg Gly Val Pro Glu Tyr Gly Cys Val Val Asn
            900                 905                 910

Leu Arg Lys Thr Val Val Asn Phe Pro Val Glu Asp Glu Ala Leu Gly
            915                 920                 925

Gly Thr Ala Phe Val Gln Met Pro Ala His Gly Leu Phe Pro Trp Cys
930                 935                 940

Gly Leu Leu Leu Asp Thr Arg Thr Ala Glu Val Gln Ser Asp Tyr Ser
945                 950                 955                 960

Ser Tyr Ala Arg Thr Ser Ile Arg Ala Ser Leu Thr Phe Asn Arg Gly
                965                 970                 975

Phe Lys Ala Gly Arg Asn Met Arg Lys Leu Phe Gly Val Leu Arg
            980                 985                 990

Leu Met Cys His Ser Leu Phe Leu Asp Leu Gln Val Asn Ser Leu Gln
            995                 1000                1005

Thr Tyr Cys Thr Asn Ile Tyr Lys Ile Leu Leu Leu Gln Ala Tyr
    1010                1015                1020

Arg Phe His Ala Cys Val Leu Gln Leu Tyr Phe His Gln Gln Val
    1025                1030                1035

Trp Lys Asn Pro Thr Phe Phe Leu Arg Val Ile Ser Asp Thr Ala
    1040                1045                1050

Ser Leu Cys Tyr Ser Ile Leu Lys Ala Lys Asn Ala Gly Met Ser
    1055                1060                1065

Leu Gly Ala Lys Gly Ala Ala Gly Pro Leu Pro Ser Glu Ala Val
    1070                1075                1080

Gln Trp Leu Cys His Gln Ala Phe Leu Leu Lys Leu Thr Arg His
    1085                1090                1095

Arg Val Thr Tyr Val Pro Leu Leu Gly Ser Leu Arg Thr Ala Gln
    1100                1105                1110
```

-continued

Thr Gln Leu Ser Arg Lys Leu Pro Gly Thr Thr Leu Thr Ala Leu
    1115                1120                1125

Glu Ala Ala Ala Asn Pro Ala Leu Pro Ser Asp Phe Lys Thr Ile
    1130                1135                1140

Leu Asp
    1145

<210> SEQ ID NO 29
<211> LENGTH: 1145
<212> TYPE: PRT
<213> ORGANISM: Homo sapiens

<400> SEQUENCE: 29

Met Pro Arg Ala Pro Arg Cys Arg Ala Val Arg Ser Leu Leu Arg Ser
1               5                   10                  15

His Tyr Ala Glu Val Arg Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Met Gly Ser Gly Ala Trp Gly Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

```
Asp Lys Glu Gln Leu Arg Pro Ser Phe Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
            405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Arg Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Met Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Tyr Leu Leu Arg Ser Phe
545                 550                 555                 560

Phe Tyr Val Tyr Glu Thr Thr Phe Gln Lys Asn Tyr Leu Phe Phe Tyr
                565                 570                 575

Met Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Tyr Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Tyr Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Met Val Ile Ala Ser Ile Ile Lys Pro Gln
                725                 730                 735

Asn Thr Tyr Cys Val Met Arg Tyr Ala Val Val Gln Lys Ala Ala His
            740                 745                 750
```

Gly His Val Arg Lys Ala Phe Lys Ser His Val Ser Asp Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Met Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Asp Leu Cys Ser Leu Cys Tyr Met Asp
        835                 840                 845

Met Glu Asn Lys Leu Phe Ala Gly Ile Arg Arg Asp Gly Leu Leu Leu
    850                 855                 860

Arg Leu Gln Tyr Ile Lys Ala Asn Ser Lys Glu Phe Ile Gly Ile Thr
865                 870                 875                 880

Glu Leu Phe Leu Leu Val Arg Pro His Leu Thr His Ala Lys Thr Phe
                885                 890                 895

Leu Arg Thr Leu Val Arg Gly Val Pro Glu Tyr Gly Cys Val Val Asn
            900                 905                 910

Leu Arg Lys Thr Val Val Asn Phe Pro Val Glu Asp Glu Ala Leu Gly
        915                 920                 925

Gly Thr Ala Phe Val Gln Met Pro Ala His Gly Leu Phe Pro Trp Cys
    930                 935                 940

Gly Leu Leu Leu Asp Thr Arg Thr Ala Glu Val Gln Ser Asp Tyr Ser
945                 950                 955                 960

Ser Tyr Ala Arg Thr Ser Ile Arg Ala Ser Leu Thr Phe Asn Arg Gly
                965                 970                 975

Phe Lys Ala Gly Arg Asn Met Arg Arg Lys Leu Phe Gly Val Leu Arg
            980                 985                 990

Leu Met Cys His Ser Leu Phe Leu Asp Leu Gln Val Asn Ser Leu Gln
        995                 1000                1005

Thr Tyr Cys Thr Asn Ile Tyr Lys Ile Leu Leu Leu Gln Ala Tyr
    1010                1015                1020

Arg Phe His Ala Cys Val Leu Gln Leu Tyr Phe His Gln Gln Val
    1025                1030                1035

Trp Lys Asn Pro Thr Phe Phe Leu Arg Val Ile Ser Asp Thr Ala
    1040                1045                1050

Ser Leu Cys Tyr Ser Ile Leu Lys Ala Lys Asn Ala Gly Met Ser
    1055                1060                1065

Leu Gly Ala Lys Gly Ala Ala Gly Pro Leu Pro Ser Glu Ala Val
    1070                1075                1080

Gln Trp Leu Cys His Gln Ala Phe Leu Leu Lys Leu Thr Arg His
    1085                1090                1095

Arg Val Thr Tyr Val Pro Leu Leu Gly Ser Leu Arg Thr Ala Gln
    1100                1105                1110

Thr Gln Leu Ser Arg Lys Leu Pro Gly Thr Thr Leu Thr Ala Leu
    1115                1120                1125

Glu Ala Ala Ala Asn Pro Ala Leu Pro Ser Asp Phe Lys Thr Ile
    1130                1135                1140

Leu Asp
    1145

```
<210> SEQ ID NO 30
<211> LENGTH: 14
<212> TYPE: PRT
<213> ORGANISM: Clostridium tetani

<400> SEQUENCE: 30

Gln Tyr Ile Lys Ala Asn Ser Lys Phe Ile Gly Ile Thr Glu
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Lys Phe Val Ala Ala Trp Thr Leu Lys Ala Ala Ala
1               5                   10

<210> SEQ ID NO 32
<211> LENGTH: 19
<212> TYPE: PRT
<213> ORGANISM: Plasmodium sp.

<400> SEQUENCE: 32

Glu Lys Lys Ile Ala Lys Met Glu Lys Ala Ser Ser Val Phe Asn Val
1               5                   10                  15

Val Asn Ser

<210> SEQ ID NO 33
<211> LENGTH: 20
<212> TYPE: PRT
<213> ORGANISM: Plasmodium sp.

<400> SEQUENCE: 33

Ile Glu Lys Lys Ile Ala Lys Met Glu Lys Ala Ser Ser Val Phe Asn
1               5                   10                  15

Val Val Asn Ser
            20

<210> SEQ ID NO 34
<211> LENGTH: 21
<212> TYPE: PRT
<213> ORGANISM: Plasmodium sp.

<400> SEQUENCE: 34

Asp Ile Glu Lys Lys Ile Ala Lys Met Glu Lys Ala Ser Ser Val Phe
1               5                   10                  15

Asn Val Val Asn Ser
            20

<210> SEQ ID NO 35
<211> LENGTH: 20
<212> TYPE: PRT
<213> ORGANISM: Plasmodium sp.

<400> SEQUENCE: 35

Asp Ile Glu Lys Lys Ile Ala Lys Met Glu Lys Ala Ser Ser Val Phe
1               5                   10                  15

Asn Val Val Asn
            20
```

<210> SEQ ID NO 36
<211> LENGTH: 19
<212> TYPE: PRT
<213> ORGANISM: Plasmodium sp.

<400> SEQUENCE: 36

Asp Ile Glu Lys Lys Ile Ala Lys Met Glu Lys Ala Ser Ser Val Phe
1               5                   10                  15

Asn Val Val

<210> SEQ ID NO 37
<211> LENGTH: 18
<212> TYPE: PRT
<213> ORGANISM: Plasmodium sp.

<400> SEQUENCE: 37

Asp Ile Glu Lys Lys Ile Ala Lys Met Glu Lys Ala Ser Ser Val Phe
1               5                   10                  15

Asn Val

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      Chimeric-tetanus toxoid; diphtheria toxoid sequence

<400> SEQUENCE: 38

Ile Leu Met Gln Tyr Ile Lys Ala Asn Ser Lys Phe Ile Gly Ile
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic Chimeric-tetanus toxoid; diphtheria toxoid sequence

<400> SEQUENCE: 39

Gln Ser Ile Ala Leu Ser Ser Leu Met Val Ala Gln Ala Ile Pro
1 5 10 15

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic Chimeric-tetanus toxoid; diphtheria toxoid sequence

<400> SEQUENCE: 40

Ile Leu Met Gln Tyr Ile Lys Ala Asn Ser Lys Phe Ile Gly Ile Pro
1 5 10 15

Met Gly Leu Pro Gln Ser Ile Ala Leu Ser Ser Leu Met Val Ala Gln
20 25 30

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic Chimeric-tetanus toxoid; diphtheria toxoid sequence

<400> SEQUENCE: 41

Ile Leu Met Gln Tyr Ile Lys Ala Asn Ser Lys Phe Ile Gly Ile Lys
1               5                   10                  15

Val Ser Arg Gln Ser Ile Ala Leu Ser Ser Leu Met Val Ala Gln
            20                  25                  30

<210> SEQ ID NO 42
<211> LENGTH: 15
<212> TYPE: PRT
<213> ORGANISM: Hepatitis C virus

<400> SEQUENCE: 42

Lys Val Leu Val Leu Asn Pro Ser Val Ala Ala Thr Leu Gly Phe
1               5                   10                  15

<210> SEQ ID NO 43
<211> LENGTH: 15
<212> TYPE: PRT
<213> ORGANISM: BK Virus

<400> SEQUENCE: 43

Pro Thr His Phe Lys Tyr His Glu Lys His Tyr Tyr Asn Ala Gln
1               5                   10                  15

<210> SEQ ID NO 44
<211> LENGTH: 15
<212> TYPE: PRT
<213> ORGANISM: Human papilloma virus

<400> SEQUENCE: 44

Leu Phe Val Val Tyr Arg Asp Ser Ile Pro His Ala Ala Cys His
1               5                   10                  15

<210> SEQ ID NO 45
<211> LENGTH: 15
<212> TYPE: PRT
<213> ORGANISM: Human papilloma virus

<400> SEQUENCE: 45

Gly Leu Tyr Asn Leu Leu Ile Arg Cys Leu Arg Cys Gln Lys Pro
1               5                   10                  15

<210> SEQ ID NO 46
<211> LENGTH: 15
<212> TYPE: PRT
<213> ORGANISM: Dengue virus

<400> SEQUENCE: 46

Gly Lys Thr Val Trp Phe Val Pro Ser Ile Lys Ala Gly Asn Asp
1               5                   10                  15

<210> SEQ ID NO 47
<211> LENGTH: 15
<212> TYPE: PRT
<213> ORGANISM: Dengue virus

<400> SEQUENCE: 47

Met Tyr Phe His Arg Arg Asp Leu Arg Leu Ala Ser Asn Ala Ile
1               5                   10                  15

<210> SEQ ID NO 48
<211> LENGTH: 17
<212> TYPE: PRT

-continued

<213> ORGANISM: Dengue virus

<400> SEQUENCE: 48

Val Glu Arg Leu Lys Arg Met Ala Ile Ser Gly Asp Asp Cys Val Val
1 5 10 15

Lys

<210> SEQ ID NO 49
<211> LENGTH: 17
<212> TYPE: PRT
<213> ORGANISM: Dengue virus

<400> SEQUENCE: 49

Ala Asn Ala Ile Phe Lys Leu Thr Tyr Gln Asn Lys Val Val Lys Val
1 5 10 15

Gln

<210> SEQ ID NO 50
<211> LENGTH: 15
<212> TYPE: PRT
<213> ORGANISM: Dengue virus

<400> SEQUENCE: 50

Ala Ser Ile Ala Ala Arg Gly Tyr Ile Ser Thr Arg Val Gly Met
1 5 10 15

<210> SEQ ID NO 51
<211> LENGTH: 17
<212> TYPE: PRT
<213> ORGANISM: Dengue virus

<400> SEQUENCE: 51

Asp Glu Asn Pro Tyr Lys Thr Trp Ala Tyr His Gly Ser Tyr Glu Val
1 5 10 15

Lys

<210> SEQ ID NO 52
<211> LENGTH: 15
<212> TYPE: PRT
<213> ORGANISM: Dengue virus

<400> SEQUENCE: 52

Glu Ala Ala Ala Ile Phe Met Thr Ala Thr Pro Pro Gly Thr Ala
1 5 10 15

<210> SEQ ID NO 53
<211> LENGTH: 17
<212> TYPE: PRT
<213> ORGANISM: Dengue virus

<400> SEQUENCE: 53

Met Val Thr Gln Met Ala Met Thr Asp Thr Thr Pro Phe Gly Gln Gln
1 5 10 15

Arg

<210> SEQ ID NO 54
<211> LENGTH: 15
<212> TYPE: PRT
<213> ORGANISM: Dengue virus

```
<400> SEQUENCE: 54

Lys Lys Arg Asn Leu Thr Ile Met Asp Leu His Pro Gly Ser Gly
1               5                   10                  15

<210> SEQ ID NO 55
<211> LENGTH: 15
<212> TYPE: PRT
<213> ORGANISM: Measles virus

<400> SEQUENCE: 55

Leu Ser Glu Ile Lys Gly Val Ile Val His Arg Leu Glu Gly Val
1               5                   10                  15

<210> SEQ ID NO 56
<211> LENGTH: 40
<212> TYPE: DNA
<213> ORGANISM: Homo sapiens

<400> SEQUENCE: 56
cccgacccct cccgggtccc cggcccagcc ccctccgggc                           40
```